United States Patent
Zhao

(10) Patent No.: US 8,110,559 B2
(45) Date of Patent: *Feb. 7, 2012

(54) HINDERED ESTER-BASED BIODEGRADABLE LINKERS FOR OLIGONUCLEOTIDE DELIVERY

(75) Inventor: Hong Zhao, Edison, NJ (US)

(73) Assignee: Enzon Pharmaceuticals, Inc., Bridgewater, NJ (US)

(*) Notice: Subject to any disclaimer, the term of this patent is extended or adjusted under 35 U.S.C. 154(b) by 102 days.

This patent is subject to a terminal disclaimer.

(21) Appl. No.: 12/402,743

(22) Filed: Mar. 12, 2009

(65) Prior Publication Data

US 2010/0234444 A1    Sep. 16, 2010

Related U.S. Application Data

(63) Continuation of application No. PCT/US2007/078597, filed on Sep. 15, 2007.

(60) Provisional application No. 60/845,028, filed on Sep. 15, 2006.

(51) Int. Cl.
*A61K 31/70* (2006.01)
*A61K 31/7052* (2006.01)
*C07H 21/04* (2006.01)

(52) U.S. Cl. .................. 514/44; 536/24.5; 536/23.1

(58) Field of Classification Search .......... None
See application file for complete search history.

(56) References Cited

U.S. PATENT DOCUMENTS

| | | | |
|---|---|---|---|
| 4,904,582 A | 2/1990 | Tullis | |
| 5,614,549 A | 3/1997 | Greenwald et al. | |
| 5,643,575 A * | 7/1997 | Martinez et al. | 424/194.1 |
| 5,707,813 A | 1/1998 | Dandliker et al. | |
| 5,840,900 A | 11/1998 | Greenwald et al. | |
| 5,880,131 A | 3/1999 | Greenwald et al. | |
| 5,965,566 A | 10/1999 | Greenwald et al. | |
| 6,127,355 A | 10/2000 | Greenwald et al. | |
| 6,303,569 B1 * | 10/2001 | Greenwald et al. | 514/1.3 |
| 6,376,470 B1 | 4/2002 | Greenwald et al. | |
| 6,887,906 B1 | 5/2005 | Teng et al. | |
| 7,037,646 B1 * | 5/2006 | Cook et al. | 435/6 |
| 7,087,229 B2 | 8/2006 | Zhao et al. | |
| 7,595,304 B2 * | 9/2009 | Zhao et al. | 514/44 R |
| 2005/0197290 A1 | 9/2005 | Zhao et al. | |

FOREIGN PATENT DOCUMENTS

| WO | 01/13958 | 3/2001 |
|---|---|---|
| WO | 2008/034119 | 3/2008 |
| WO | 2008/034123 | 3/2008 |

OTHER PUBLICATIONS

Dias et al., European Journal of Pharmaceutics and Biopharmaceutics, vol. 54, (2002), p. 263-269.*
International Search Report and Written Opinion issued in PCT/US2007/78597 and dated Aug. 14, 2008.
Zhao, H., et al. Bioconjugate Chem. 2005, 16:758-766.
Oishi, M., et al. J.A.C.S. 2005, 127:1624-1625.
Harris, et al., J. Pharmaceutical Science, 1998, 87:1440-1445.

* cited by examiner

*Primary Examiner* — Yong Chu
(74) *Attorney, Agent, or Firm* — Lucas & Mercanti, LLP

(57) ABSTRACT

The invention provides hindered ester-based biodegradable linkers for the delivery of oligonucleotides in vivo, as well as method of making and using the same.

16 Claims, 4 Drawing Sheets

SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: Thiobackbone
<220> FEATURE:
<221> NAME/KEY: modified_base
<222> LOCATION: (1)
<223> OTHER INFORMATION: Methylated cytosine
<220> FEATURE:
<221> NAME/KEY: misc_feature
<222> LOCATION: (1)
<223> OTHER INFORMATION: LNA
<220> FEATURE:
<221> NAME/KEY: misc_feature
<222> LOCATION: (2)
<223> OTHER INFORMATION: LNA
<220> FEATURE:
<221> NAME/KEY: modified_base
<222> LOCATION: (3)
<223> OTHER INFORMATION: Methylated cytosine
<220> FEATURE:
<221> NAME/KEY: misc_feature
<222> LOCATION: (3)
<223> OTHER INFORMATION: LNA
<220> FEATURE:
<221> NAME/KEY: misc_feature
<222> LOCATION: (4)
<223> OTHER INFORMATION: LNA
<220> FEATURE:
<221> NAME/KEY: modified_base
<222> LOCATION: (13)
<223> OTHER INFORMATION: Methylated cytosine
<220> FEATURE:
<221> NAME/KEY: misc_feature
<222> LOCATION: (13)
<223> OTHER INFORMATION: LNA
<220> FEATURE:
<221> NAME/KEY: misc_feature
<222> LOCATION: (14)
<223> OTHER INFORMATION: LNA
<220> FEATURE:
<221> NAME/KEY: misc_feature
<222> LOCATION: (15)
<223> OTHER INFORMATION: LNA

<400> SEQUENCE: 1
ctcaatccat ggcagc                                                       16

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      Oligonucleotide
<220> FEATURE:
<221> NAME/KEY: misc_feature
<222> LOCATION: (1)..(19)
<223> OTHER INFORMATION: RNA

<400> SEQUENCE: 2
gcaugcggcc ucuguuugat t                                                 21

```
<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)   (19)
<223> OTHER INFORMATION: RNA

<400> SEQUENCE: 3
ucaaacagag gccgcaugct t                                               21

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Thiobackbone

<400> SEQUENCE: 4
tctcccagcg tgcgccat                                                   18

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)   (16)
<223> OTHER INFORMATION: Thiobackbone
<220> FEATURE:
<221> NAME/KEY: misc_feature
<222> LOCATION: (1)   (3)
<223> OTHER INFORMATION: LNA
<220> FEATURE:
<221> NAME/KEY: misc_feature
<222> LOCATION: (13)   (15)
<223> OTHER INFORMATION: LNA

<400> SEQUENCE: 5
tggcaagcat cctgta                                                     16
```

HINDERED ESTER-BASED BIODEGRADABLE LINKERS FOR OLIGONUCLEOTIDE DELIVERY

CROSS-REFERENCE TO RELATED APPLICATION

This patent application is a continuation of PCT/US2007/078597 filed Sep. 15, 2007, which claims the benefit of priority from. U.S. Provisional Patent Application No. 60/845,028 filed Sep. 15, 2006, the contents of each of which are incorporated herein by reference.

FIELD OF THE INVENTION

The invention provides ester-based biodegradable linkers for the delivery of oligonucleotides in vivo.

BACKGROUND OF THE INVENTION

Classical therapeutic interventions in medicine have typically focused upon interactions with bodily proteins, such as receptors, enzymes, hormones and the like, in efforts to moderate their disease-causing or disease potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides that are complementary to a specific target messenger RNA (mRNA) sequence. Generally, nucleic acid sequences complementary to the products of gene transcription (e.g., mRNA) are designated "antisense", and nucleic acid sequences having the same sequence as the transcript or being produced as the transcript are designated "sense". See, e.g., Crooke, 1992, *Annu. Rev. Pharmacol. Toxicol*, 32:329-376. An antisense oligonucleotide can be selected to hybridize to all or part of a gene, in such a way as to modulate expression of the gene. Transcription factors interact with double-stranded DNA during regulation of transcription. Oligonucleotides can serve as competitive inhibitors of transcription factors to modulate their action. Several recent reports describe such interactions (see Bielinska, A., et al., 1990, *Science,* 250: 997-1000; and Wu, H., et al., 1990, *Gene* 89: 203-209).

Molecular strategies are being developed to down-regulate unwanted gene expression. Recently, the use of modified oligonucleotide compounds has developed into a promising method of treatment against such diseases as viral infections, inflammatory and genetic disorder and significantly, cancer. Antisense DNAs were first conceived as alkylating complementary oligodeoxynucleotides directed against naturally occurring nucleic acids (Belikova, et al., *Tetrahedron Lett.* 37:3557-3562, 1967). Zamecnik and Stephenson were the first to propose the use of synthetic antisense oligonucleotides for therapeutic purposes. (Zamecnik & Stephenson, 1978, *Proc. Natl. Acad. Sci. U.S.A.,* 75:285-289; Zamecnik & Stephenson, 1978, *Proc. Natl. Acad. Sci. U.S.A.,* 75:280-284). They reported that the use of an oligonucleotide 13-mer complementary to the RNA of Rous sarcoma virus inhibited the growth of the virus in cell culture. Since then, numerous other studies have been published manifesting the in vitro efficacy of antisense oligonucleotide inhibition of viral growth, e.g., vesicular stomatitis viruses (Leonetti et al., 1988, *Gene,* 72:323), herpes simplex viruses (Smith et al., 1987, *Proc. Natl. Acad. Sci. U.S.A.* 83:2787), and influenza virus (Seroa; et al., 1987, *Nucleic Adds Res.* 15:9909).

Oligonucleotides have also found use in among others, diagnostic tests, research reagents e.g. primers in PCR technology and other laboratory procedures. Oligonucleotides can be custom synthesized to contain properties that are tailored to fit a desired use. Thus numerous chemical modifications have been introduced into oligomeric compounds to increase their usefulness in diagnostics, as research reagents and as therapeutic entities.

Although oligonucleotides, especially antisense oligonucleotides show promise as therapeutic agents, they are very susceptible to nucleases and can be rapidly degraded before and after they enter the target cells making unmodified antisense oligonucleotides unsuitable for use in in vivo systems. Because the enzymes responsible for the degradation are found in most tissues, modifications to the oligonucleotides have been made in an attempt to stabilize the compounds and remedy this problem. The most widely tested modifications have been made to the back-bone portion of the oligonucleotide compounds. See generally Uhlmann and Peymann, 1990, *Chemical Reviews* 90, at pages 545-561 and references cited therein. Among the many different back bones made, only phosphorothioate showed significant antisense activity. See for example, Padmapriya and Agrawal, 1993, *Bioorg. & Med. Chem. Lett.* 3, 761. While the introduction, of sulfur atoms to the back bone slows the enzyme degradation rate, it also increases toxicity at the same time. Another disadvantage of adding sulfur atoms is that it changes the back bone from achiral to chiral and results in $2^n$ diastereomers. This may cause further side effects. Still more disadvantages of present antisense oligonucleotides are that they may carry a negative charge on the phosphate group which inhibits its ability to pass through the mainly lipophilic cell membrane. The longer the compound remains outside the cell, the more degraded it becomes resulting in less active compound arriving at the target. A further disadvantage of present antisense compounds is that oligonucleotides tend to form secondary and high-order solution structures. Once these structures are formed, they become targets of various enzymes, proteins, RNA, and DNA for binding. This results in nonspecific side effects and reduced amounts of active compound binding to mRNA. Other attempts to improve oligonucleotide therapy have included adding a linking moiety and polyethylene glycol. See for example, Kawaguchi, et al., Stability, Specific Binding Activity, and Plasma Concentration in Mice of an Oligodeoxynucleotide Modified at 5'-Terminal with Poly (ethylene glycol), *Biol. Pharm. Bull.,* 18(3) 474-476 (1995), and U.S. Pat. No. 4,904,582. In both of these examples, the modifications involve the use of linking moieties that are permanent in nature in an effort to stabilize the oligonucleotide against degradation and increase cell permeability. However, both of these efforts fail to provide any efficacy.

More recently, in co-owned U.S. Ser. No. 10/822,205, incorporated by reference herein in its entirety, amino-releasable polymer conjugated oligonucleotides have been provided. However, it would, be even more desirable to release the oligonucleotide in plasma in a controlled fashion without the necessity for an amino-tail linker.

Due to the inadequacies of the present methods, there exists a need to improve stability and resistance to nuclease degradation as well as decrease toxicity and increase binding affinity to mRNA of oligonucleotide compounds. The current oligonucleotide therapy is expensive. This is mainly due to the degradation problem. Thus, there is a real need to protect the antisense oligonucleotide compounds against degradation, prevent the formation of high-order structures and at the same time deliver sufficient amounts of active antisense oligonucleotide compounds to the target. This invention provides such improvements.

SUMMARY OF THE INVENTION

In one aspect of the present invention, the present invention provides compounds for the in vivo delivery of polynucleotides, such as oligonucleotides, that include a structure according to Formula (I)

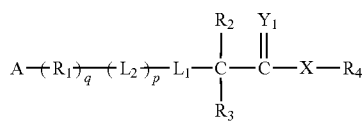

wherein
A is a capping group or

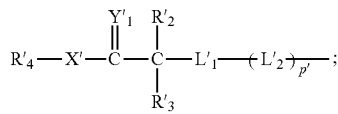

$R_1$ is a substantially non-antigenic water-soluble polymer;
$L_1$ and $L'_1$ are independently selected spacers having a free electron pair positioned four to ten atoms from $C(=Y_1)$ or $C(=Y'_1)$, preferably from about 4 to about 8, and most preferably from about 4 to about 5 atoms from $C(=Y_1)$ or $C(=Y'_1)$;
$L_2$ and $L'_2$ are independently selected bifunctional linkers;
$Y_1$ and $Y'_1$ are independently O, S, or $NR_5$;
X and X' are independently O or S;
$R_2$, $R'_2$, $R_3$, $R'_3$ and $R_5$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substitated alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy, or $R_2$ together with $R_3$ and $R'_2$ together with $R'_3$ independently form a substituted or unsubsituted non-aromatic cyclohydrocarbon containing at least three carbons;
$R_4$ and $R'_4$ are independently selected polynucleotides and derivatives thereof;
(p) and (p') are independently zero or a positive integer, preferably zero or an integer from about 1 to about 3, more preferably zero or 1; and
(q) and (q') are independently zero or 1,
provided that $R_3$ is a substituted or unsubstituted hydrocarbon having at least three carbons when $R_2$ is H, and further provided that $L_1$ is not the same as $C(R_2)(R_3)$.
In certain preferred embodiments of this aspect of the invention, the substantially non-antigenic polymer is a polyalkylene oxide and is more preferably polyethylene glycol (hereinafter PEG). In other aspects, the PEG is either capped on one terminal with a $CH_3$ group, i.e. mPEG, while in other embodiments, bis-activated PEGs are provided such as those corresponding to the formula:

Further aspects of the invention include methods of methods of making conjugates containing the hindered ester as well as methods of treatment based on administering effective amounts of conjugates containing a biologically active moiety to a patient (mammal) in need thereof. Methods of delivering the conjugate to cells requiring such treatment are also included.

The polymeric delivery systems described herein include novel linkers which can form a releasable bond such as an ester bond between the polymer and biologically active moiety such as oligonucleotides. While the hindered ester of oligonucleotides is stable during the storage, it can release the native oligonucleotides without any tails by hydrolyzing the phosphodiester or phosphothioester bonds. In addition, the polymeric compound of the invention can facilitate hydrolysis of the stable hindered ester bond by anchimeric assistance from the linkers.

One advantage of the hindered ester-based polymeric transport systems described herein is that the polymeric delivery systems have improved stability. Without being bound by any theories, the ester bond in a sterically hindered environment between the polymer and a moiety such as an oligonucleotide can inhibit the ester linkage from being exposed to basic aqueous medium or enzymes, and thereby stabilizes the covalent linkage. The stability of the polymeric systems allows longer shelf life for the polymeric conjugate. The improved stability increases cost efficiency.

The polymeric delivery systems described herein are especially well suited for use with oligonucleotides and related antisense, short-interfering RNA (siRNA), or locked nucleic add (LNA) compounds. The presence of the hindered ester group in proximity to the oligonucleotide attached thereto provides improved stability and resistance to nuclease degradation. It also helps decrease toxicity and increase binding affinity to mRNA of oligonucleotide compounds. Conjugates made in accordance with the invention provide a means for protecting antisense oligonucleotide compounds against degradation, preventing the formation of high-order structures. Moreover, the polymer conjugates allow the artisan to deliver sufficient amounts of active antisense oligonucleotide compounds to the target.

The inventive linker is stable under all the buffer conditions suitable for animal or human intravenous administration in aqueous form. The inventive linker will hydrolyze to release the intact oligonucleotide in plasma in the presence of plasma enzymes. Variation of the steric hinderance on the linker will modify the rate of hydrolysis, as required for particular delivery systems.

Another advantage of the activated polymers containing the hindered esters is that it allows the artisan to more easily conjugate oligonucleotides of choice. There is no need to modify the oligonucleotide or target moiety with the hindered ester before PEGylation. The oligonucleotides is taken as is and PEGylated with the activated PEG linker which contains the desired hindered ester protective group thereon.

Further advantage is that the inventive linker can be conjugated with any of the nucleotides (A, G, C, T, U etc) and then converted to its phosphoamidite, for example. The phosphoamidite can then be employed under normal solid phase oligonucleotide synthesis conditions to make oligonucleotide molecules. The linkage between the linker and the oligonucleotide is stable under the conditions needed for synthesis and purification.

Other and further advantages will be apparent from the following description.

For purposes of the present invention, the term "residue" shall be understood to mean that portion of a biologically active compound, such as an oligonucleotide, which remains after it has undergone a reaction in which the prodrug carrier portion has been attached by modification of e.g., an available hydroxyl or amino group, to form, for example, an ester or amide group, respectively. Analogously, the residue of a substantially non-antigenic polymer, e.g., a polyalkylene oxide polymer, is that portion of the polymer that remains after it has undergone a reaction in which the polymer has been attached to a linker, spacer and/or biologically active compound or residues thereof.

For purposes of the present invention, the use of the singular or plural is not meant to be limiting of the numerical number of the referenced item or object. Thus, the use of the singular to refer to a cell, polymer or drug does not imply that only one cell is treated, only one molecule is prepared or employed, and/or only one drug is employed, and the use of the plural does not exclude application to a single referenced item, unless expressly stated.

Unless otherwise defined, for purposes of the present invention:

the term "alkyl" shall be understood to include straight, branched, substituted, e.g. halo-, alkoxy-, and nitro- $C_{1-12}$ alkyls, $C_{3-8}$ cycloalkyls or substituted cycloalkyls, etc.;

the term "substituted" shall be understood to include adding or replacing one or more atoms contained within a functional group or compound with one or more different atoms;

the term "substituted alkyls" include carboxyalkyls, aminoalkyls, dialkylaminos, hydroxyalkyls and mercaptoalkyls;

the term "substituted cycloalkyls" include moieties such as 4-chlorocyclohexyl; aryls include moieties such as napthyl; substituted aryls include moieties such as 3-bromophenyl; aralkyls include moieties such as toluyl; heteroalkyls include moieties such as ethylthiophene;

the term "substituted heteroalkyls" include moieties such as 3-methoxy-thiophene; alkoxy includes moieties such as methoxy; and phenoxy includes moieties such as 3-nitrophenoxy;

the term "halo" shall be understood to include fluoro, chloro, iodo and bromo; and the terms "sufficient amounts" and "effective amounts" for purposes of the present invention shall mean an amount which achieves a therapeutic effect as such effect is understood by those of ordinary skill in the art.

DETAILED DESCRIPTION OF THE INVENTION

A. Overview

Figure 1:
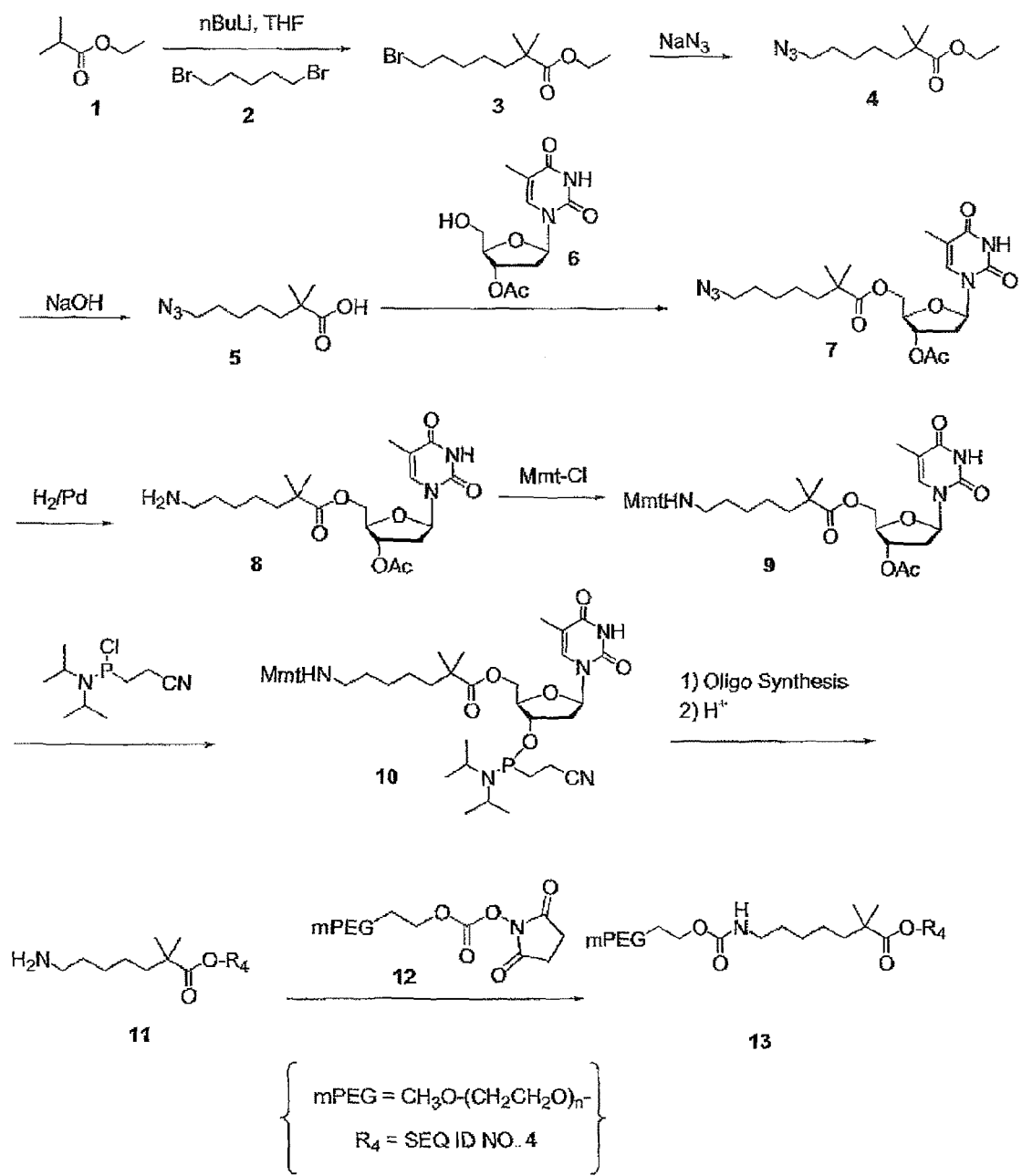
FIG. 1 schematically illustrates methods of synthesis described in Example 1-9.

The invention provides hindered ester-based biodegradable linkers for oligonucleotide delivery in vivo. Thus, the present invention provides for polymer-linked oligonucleotide prodrugs useful having many practical uses, including uses as diagnostic and analytic reagents, as research and investigational tools, both in vitro and in vivo, and as therapeutic agents. In accordance with the foregoing, there are provided compounds of Formula (I):

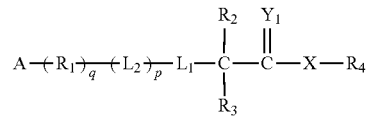

wherein
A is a capping group or

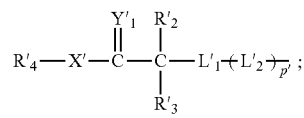

$R_1$ is a substantially non-antigenic water-soluble polymer;

$L_1$ and $L'_1$ are independently selected spacers having a free electron pair positioned four to ten atoms from $C(=Y_1)$ or $C(=Y'_1)$, preferably from about 4 to about 8, and most preferably from about 4 to about 5 atoms from $C(=Y_1)$ or $C(=Y'_1)$;

$L_2$ and $L'_2$ are independently selected bifunctional linkers;
$Y_1$ and $Y'_1$ are independently O, S, or NR5;
X and X' are independently O or S;

$R_2$, $R'_2$, $R_3$, $R'_3$ and $R_5$ are independently selected from among hydrogen, $C_{1-6}$ alkyl, $C_{2-6}$ alkenyl, $C_{2-6}$ alkynyl, $C_{3-19}$ branched alkyl, cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy, or $R_2$ together with $R_3$ and $R'_2$ together with $R'_3$ independently form a substituted or unsubsituted non-aromatic cyclohydrocarbon containing at least three carbons;

$R_4$ and $R'_4$ are independently selected polynucleotides and derivatives thereof;

(p) and (p') are independently zero or a positive integer, preferably zero or an integer from about 1 to about 3, more preferably zero or 1; and (q) and (q') are independently zero or 1,
provided that $R_3$ is a substituted or unsubstituted hydrocarbon having at least three carbons when $R_2$ is H, and further provided that $L_1$ is not the same as $C(R_2)(R_3)$.

In some aspects of the invention, the compounds described herein contain polymers according to Formula (Ia):

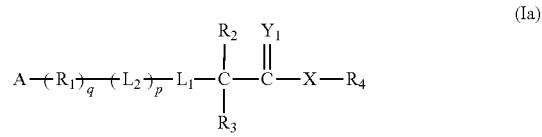

wherein, (q) is 1.

In certain preferred embodiments of this aspect of the invention, the substantially non-antigenic polymer is a polyalkylene oxide and is more preferably polyethylene glycol (hereinafter PEG). In other aspects, the PEG is either capped on one terminal with a $CH_3$ group, i.e. mPEG.

In other embodiments, bis-activated PEGs are provided such as those corresponding to Formula (II):

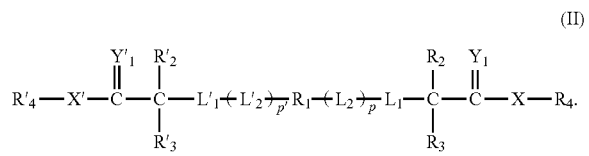

(II)

Within those aspects of the invention, the substituents contemplated for substitution, where the moieties corresponding to $R_2$, $R'_2$, $R_3$, $R'_3$ and $R_5$ are indicated as being possibly substituted can include, for example, acyl, amino, amido, amidine, ara-alkyl, aryl, azido, alkylmercapto, arylmercapto, carbonyl, carboxylate, cyano, ester, ether, formyl, halogen, heteroaryl, heterocycloalkyl, hydroxy, imino, nitro, thiocarbonyl, thioester, thioacetate, thioformate, alkoxy, phosphoryl, phosphonate, phosphinate, silyl, sulfhydryl, sulfate, sulfonate, sulfamoyl, sulfonamide, and sulfonyl.

Preferably, $L_1$ and $L'_1$ are independently selected spacers having a free electron pair positioned four to eight atoms from $C(=Y_1)$ or $C(=Y'_1)$; more preferably four to six; and both $Y_1$ and $Y'_1$ are O.

In another aspects of the invention, the polynucleotides include oligonucleotides, preferably from about 2 to about 100 oligomers, more preferably from about 3 to about 50 oligomers, most preferably from about 5 to about 30 oligomers.

In yet another aspect, A can be selected from among H, $NH_2$, OH, $CO_2H$, $C_{1-6}$ alkoxy, and $C_{1-6}$ alkyls. In some preferred embodiments, A can be methyl, ethyl, methoxy, ethoxy, H, and OH. A is more preferably methyl or methoxy.

In a further aspect, the present invention provides intermediates to extend the polynucleotide. According to this aspect, the compounds of Formula (I) further include N,N-tetraisopropyl-cyanoethyl phosphoramidite and form compounds of formula (Ib):

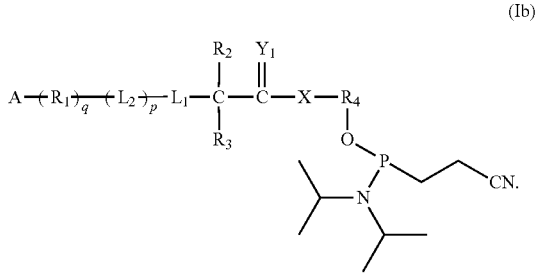

(Ib)

With respect to this aspect, preferably (q) is zero.

B. Substantially Non-Antigenic Water-Soluble Polymers

Polymers employed in the polymeric delivery systems described herein are preferably water soluble polymers and substantially non-antigenic such as polyalkylene oxides (PAO's).

In one aspect of the invention, the compounds described herein include a linear, terminally branched or multi-armed polyalkylene oxide. In some preferred embodiments, the polyalkylene oxide includes polyethylene glycol and polypropylene glycol.

The polyalkylene oxide has an average molecular weight from about 2,000 to about 100,000 daltons, preferably from about 5,000 to about 60,000 daltons. In some aspects the polyalkylene oxide can be from about 5,000 to about 25,000, and preferably from about 12,000 to about 20,000 daltons when proteins or oligonucleotides are attached or alternatively from about 20,000 to about 45,000 daltons, and preferably from about 30,000 to about 40,000 daltons when pharmaceutically active compounds (small molecules) are employed in the compounds described herein.

The polyalkylene oxide includes polyethylene glycols and polypropylene glycols. More preferably, the polyalkylene oxide includes polyethylene glycol (PEG). PEG is generally represented by the structure:

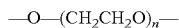

—O—$(CH_2CH_2O)_n$— where (n) is an integer from about 10 to about 2,300, and is dependent on the number of polymer arms when multi-arm polymers are used. Alternatively, the polyethylene glycol (PEG) residue portion of the invention can be selected from among:

—$Y_{71}$—$(CH_2CH_2O)_n$—$CH_2CH_2Y_{71}$—,

—$Y_{71}$—$(CH_2CH_2O)_n$—$CH_2C(=Y_{22})$—$Y_{71}$—,

—$Y_{71}$—$C(-Y_{72})$—$(CH_2)_{a2}$-$Y_{73}$—$(CH_2CH_2O)_n$—$CH_2CH_2$—$Y_{73}$—$(CH_2)_{a2}$-$C(=Y_{72})$—$Y_{71}$— and —$Y_{71}$—$(CR_{71}R_{72})_{a2}$-$Y_{73}(CH_2)_{b2}$-O—$(CH_2CH_2O)_n$—$(CH_2)_{b2}$-$Y_{73}$—$(CR_{71}R_{72})_{a2}$-$Y_{71}$—, wherein:

$Y_{71}$ and $Y_{73}$ are independently O, S, SO, $SO_2$, $NR_{73}$ or a bond;

$Y_{72}$ is O, S, or $NR_{74}$;

$R_{71-74}$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-5}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

(a2) and (b2) are independently zero or a positive integer, preferably zero or an integer from about 1 to about 6, and more preferably 1; and (n) is an integer from about 10 to about 2300.

Branched or U-PEG derivatives are described in U.S. Pat. Nos. 5,643,575, 5,919,455, 6,113,906 and 6,566,506, the disclosure of each of which is incorporated herein by reference. A non-limiting list of such polymers corresponds to polymer systems (i)-(vii) with the following structures:

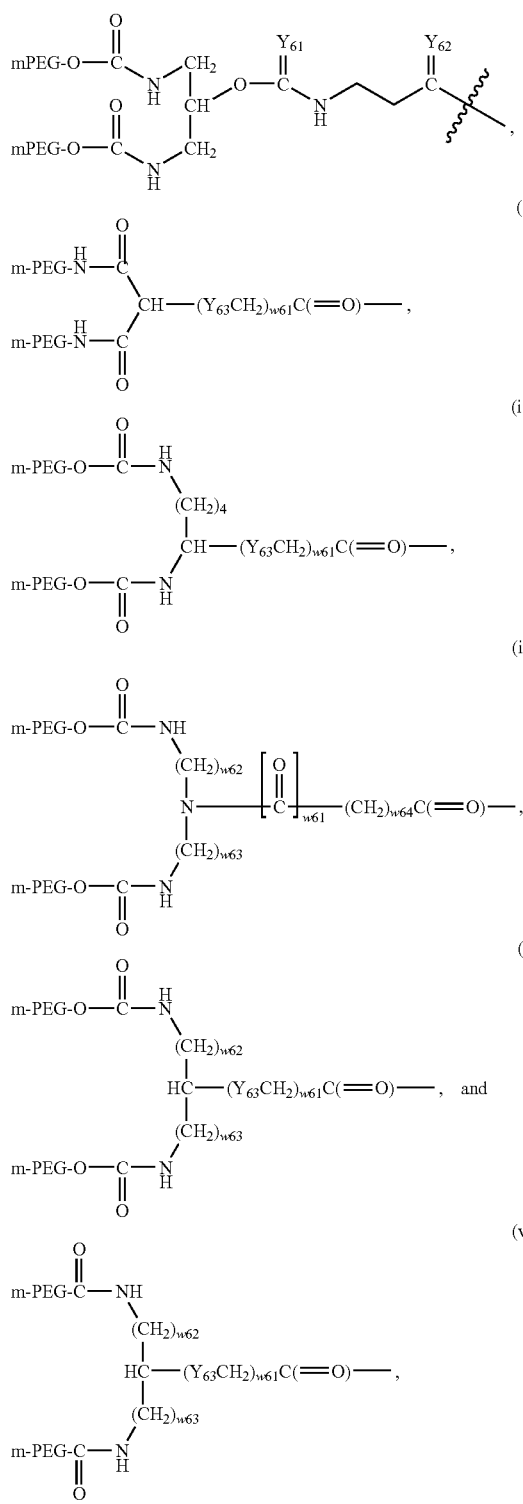

wherein:
$Y_{61-62}$ are independently O, S or $NR_{61}$;
$Y_{63}$ is O, $NR_{62}$, S, SO or $SO_2$
(w62), (w63) and (w64) are independently 0 or a positive integer, preferably zero or an integer from about 1 to about 3;
(w61) is 0 or 1;
mPEG is methoxy PEG wherein PEG is previously defined and a total molecular weight of the polymer portion is from about 2,000 to about 100,000 daltons; and
$R_{61}$ and $R_{62}$ are independently the same moieties which can be used for $R_{73}$.

In yet another aspect, the polymers include multi-arm PEG-OH or "star-PEG" products such as those described in NOF Corp. Drug Delivery System catalog, Ver. 8, April 2006, the disclosure of which is incorporated herein by reference. The multi-arm polymer conjugates contain four or more polymer arms and preferably four or eight polymer arms.

For purposes of illustration and not limitation, the multi-arm polyethylene glycol (PEG) residue can be

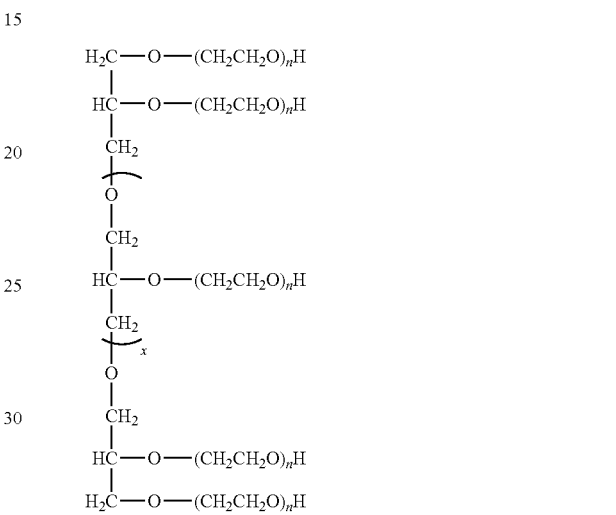

wherein:
x is 0 and a positive integer, i.e. from about 0 to about 28; and
n is the degree of polymerization.

In one particular embodiment of the present invention, the multi-arm PEG has the structure:

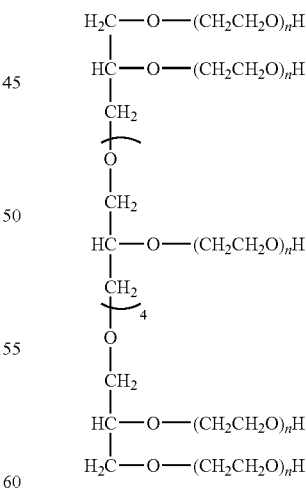

wherein n is a positive integer. In one preferred embodiment of the invention, the polymers have a total molecular weight of from about 5,000 Da to about 60,000 Da, and preferably from 12,000 Da to 40,000 Da, In yet another particular embodiment, the multi-arm PEG has the structure:

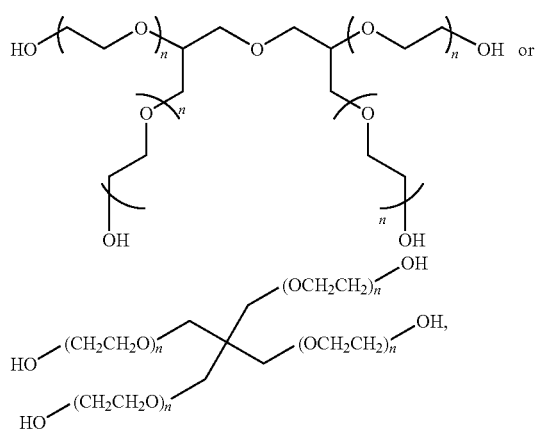

wherein n is a positive integer. In one preferred embodiment of the invention, the degree of polymerization for the multi-arm polymer (n) is from about 28 to about 350 to provide polymers having a total molecular weight of from about 5,000 Da to about 60,000 Da, and preferably from about 65 to about 270 to provide polymers having a total molecular weight of from 12,000 Da to 45,000 Da. This represents the number of repeating units in the polymer chain and is dependent on the molecular weight of the polymer.

The polymers can be converted into a suitably activated polymer, using the activation techniques described in U.S. Pat. Nos. 5,122,614 or 5,808,096 patents. Specifically, such PEG can be of the formula:

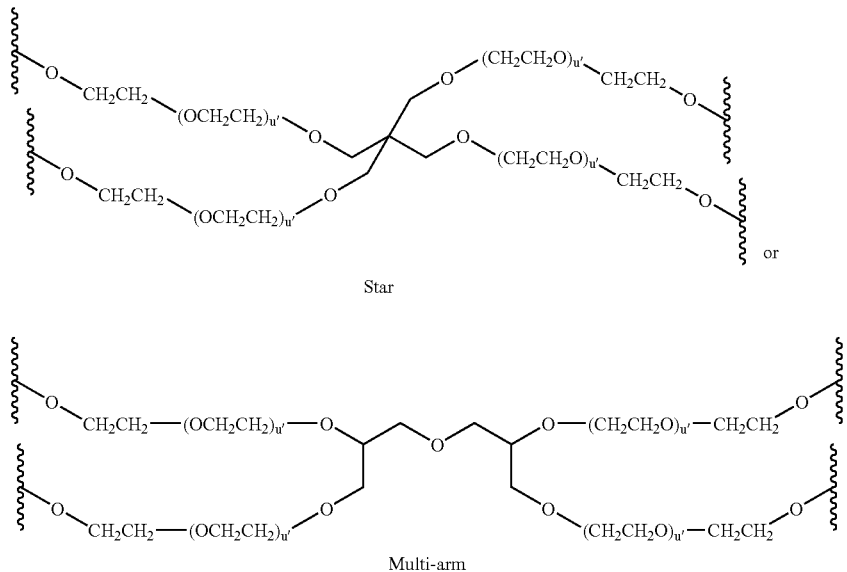

wherein:
(u') is an integer from about 4 to about 455; and up to 3 terminal portions of the residue is/are capped with a methyl or other lower alkyl.

In some preferred embodiments, all four of the PEG arms can be converted to suitable activating groups, for facilitating attachment to aromatic groups. Such compounds prior to conversion include:

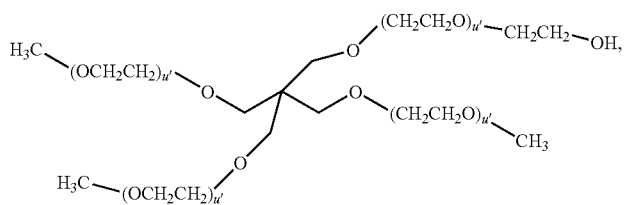

-continued
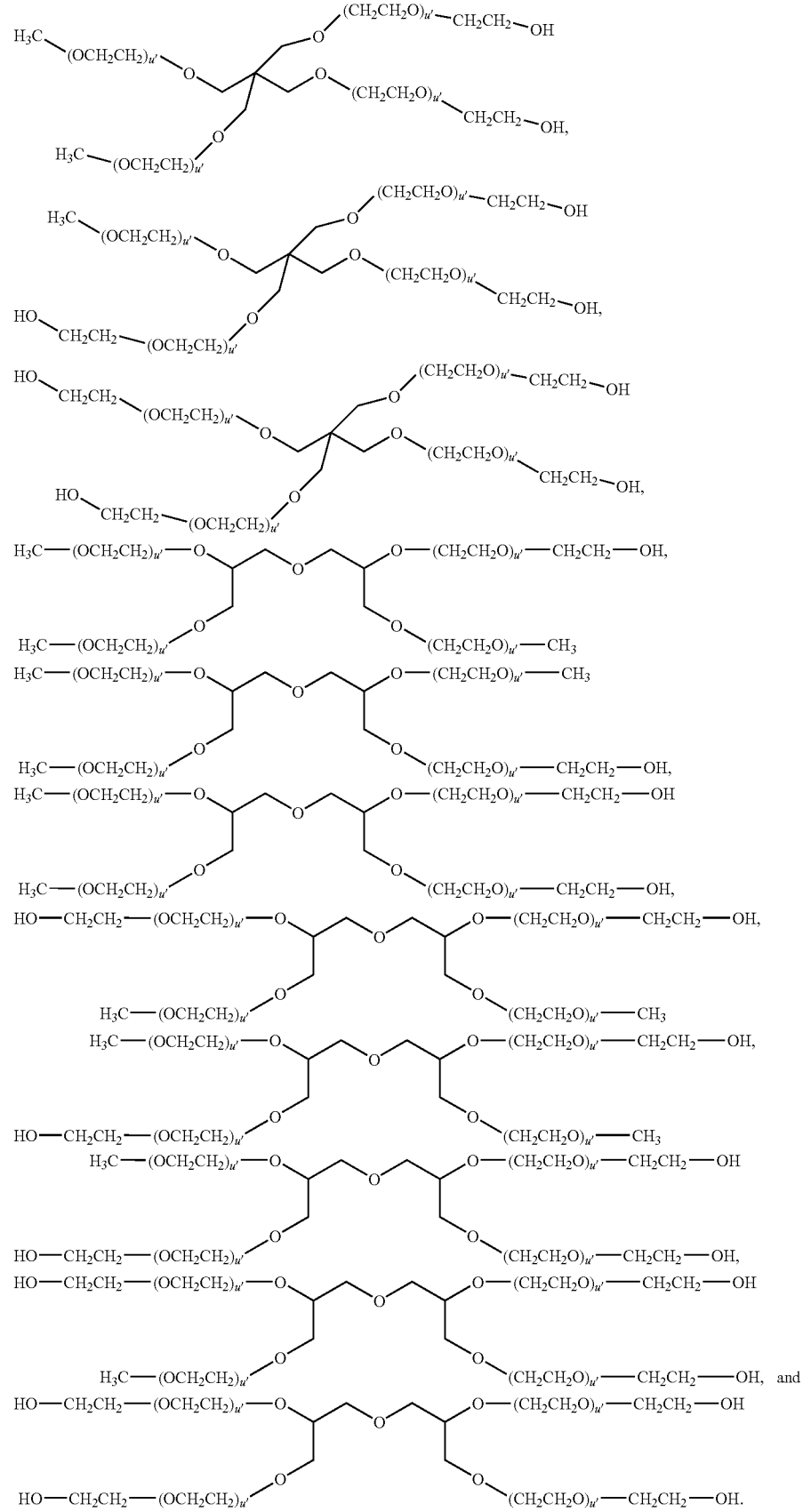

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

In a further embodiment and as an alternative to PAO-based polymers, one or more effectively non-antigenic materials such as dextran, polyvinyl alcohols, carbohydrate-based polymers, hydroxypropylmethacrylamide (HPMA), polyalkylene oxides, and/or copolymers thereof can be used. See also commonly assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated. For purposes of the present invention, "substantially or effectively non-antigenic" means all materials understood in the art as being nontoxic and not eliciting an appreciable immunogenic response in mammals.

In some aspects, polymers having terminal amine groups can be employed to make the compounds described herein. The methods of preparing polymers containing terminal amines in high purity are described in U.S. patent application Ser. Nos. 11/508,507 and 11/537,172, the contents of each of which are incorporated by reference. For example, polymers having azides react with phosphine-based reducing agent such as triphenylphosphine or an alkali metal borohydride reducing agent such as $NaBH_4$. Alternatively, polymers including leaving groups react with protected amine salts such as potassium salt of methyl-tert-butyl imidodicarbonate (KNMeBoc) or the potassium salt of di-tert-butyl imidodicarbonate ($KNBoc_2$) followed by deprotecting the protected amine group. The purity of the polymers containing the terminal amines formed by these processes is greater than about 95% and preferably greater than 99%.

In alternative aspects, polymers having terminal carboxylic acid groups can be employed in the polymeric delivery systems described herein. Methods of preparing polymers having terminal carboxylic acids in high purity are described in U.S. patent application Ser. No. 11/328,662, the contents of which are incorporated herein by reference. The methods include first preparing a tertiary alkyl ester of a polyalkylene oxide followed by conversion to the carboxylic acid derivative thereof. The first step of the preparation of the PAO carboxylic acids of the process includes forming an intermediate such as t-butyl ester of polyalkylene oxide carboxylic acid. This intermediate is formed by reacting a PAO with a t-butyl haloacetate in the presence of a base such as potassium t-butoxide. Once the t-butyl ester intermediate has been formed, the carboxylic acid derivative of the polyalkylene oxide can be readily provided in purities exceeding 92%, preferably exceeding 97%, more preferably exceeding 99% and most preferably exceeding 99.5% purity.

C. Hindered Esters

For purposes of the present invention, "hindered" shall be understood to mean or include a sterically crowded environment around the $C(=Y_1)$. Such environment can be made typically by including bulk substituents, such as cyclic or branched moieties. Each of the $CR_2R_3$ and $CR'_2R'_3$ moieties adjacent to $C(=Y_1)$ and $C(=Y'_1)$ according to Formula (I) form hindered esters. The $R_2$, $R'_2$, $R_3$, $R'_3$ and $R_5$ can be selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy. Any of the possible groups described herein for $R_2$ and $R_3$ ($R'_2$ and $R'_3$) can be used so long as both $R_2$ and $R_3$ ($R'_2$ and $R'_3$) are not simultaneously H. When one of $R_2$ and $R_3$ ($R'_2$ and $R'_3$) is H, the other contains at least three hydrocarbons.

In one preferred embodiment, $R_2$, $R'_2$, $R_3$ and $R'_3$ include methyl, ethyl and isopropyl.

In an alternative embodiment, $R_2$ together with $R_3$ and $R'_2$ together with $R'_3$ can form a substituted or unsubsituted non-aromatic cyclohydrocarbon containing at least three carbons.

D. Spacers: $L_1$ and $L'_1$

In another aspect of the present invention, free electron pairs of the $L_1$ and $L'_1$ spacers linked to the $CR_2R_3$ and $CR'_2R'_3$ moieties provide enchimeric effects. Without being bound by any theory, the free electron pairs positioned four to ten atoms from $C(=Y_1)$ and $C(=Y'_1)$ facilitate (modify) release rate of biologically active moieties, target groups and diagnostic agents from the polymeric delivery systems described herein.

In one preferred embodiment, the $L_1$ and $L'_1$ spacers can be selected from among:
- —$NR_{11}(CR_{12}R_{13})_s$—,
- —$S(CR_{12}R_{13})_s$—,
- —$O(CR_{12R13})_s$—,
- —$[C(=O)]_r(CR_{12}R_{13})_s$—,
- —$NR_{11}(CR_{12}R_{13})_sO(CR_{14}R_{15})_{s'}$—,
- —$NR_{11}(CR_{12}R_{13})_sS(CR_{14}R_{15})_{s'}$—,
- —$NR_{11}(CR_{12}R_{13})_sNR_{16}(CR_{14}R_1)_{s'}$—,
- —$NR_{11}(CR_{12}R_{13}O)_s(CR_{14}R_{15})_{s'}$—,
- —$O(CR_{12}R_{13})_sO(CR_{14}R_{15})_{s'}$—,
- —$O(CR_{12}R_{13})_sS(CR_{14}R_{15})_{s'}$—,
- —$O(CR_{12}R_{13})_sNR_{16}(CR_{14}R_{15})_{s'}$—,
- —$O(CR_{12}R_{13}O)_s(CR_{14}R_{15})_{s'}$—, wherein:

$R_{11}$-$R_{16}$ are independently selected from among hydrogen, amino, substituted amino, azido, carboxy, cyano, halo, hydroxyl, nitro, silyl ether, sulfonyl, mercapto, $C_{1-6}$ alkylmercapto, arylmercapto, substituted arylmercapto, substituted $C_{1-6}$ alkylthio, $C_{1-6}$ alkyls, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy, substituted and arylcarbonyloxy;

(s) and (s') are independently zero or a positive integer, preferably from about 1 to about 4; and (r) is 0 or 1.

Alternatively, the $L_1$ and $L'_1$ groups can be selected from among:

—NH—(CH$_2$—CH$_2$—O)$_q$—CH$_2$—, —C(=O)—(CH$_2$)$_p$—, —NH—(CH$_2$)$_p$—,
—S—(CH$_2$)$_p$—,
—NH—(CH$_2$)$_p$—O—CH$_2$— and
—NH—C(=O)—(CH$_2$)$_p$—NH—C(=O)—(CH$_2$)$_q$—
wherein (p) is an integer from about 1 to about 12, preferably from about 1 to about 8, more preferably from about 2 to about 5; and (q) are independently a positive Integer, preferably from about 1 to about 8, and more preferably from about 1 to about 4.

$L_1$ and $L'_1$ preferably include —(CH$_2$)$_{x21}$— or —(CH$_2$)$_{x21}$—W—(CH$_2$)$_{x22}$—, wherein (x21) and (x22) are integers ranging in value from 1 to 7, and W is O or NH.

In yet another preferred embodiment, the free electron pairs of the $L_{1-2}$ and $L'_{1-2}$ spacers are positioned four to eight atoms from C(=Y$_1$) and C(=Y'$_1$). More preferably, the electron pairs are positioned four to five atoms from C(=Y$_1$) and C(=Y'$_1$).

Preferred embodiments according to the preferred aspect are -L$_1$-C(R$_2$)(R$_3$)—C(=Y$_1$)— and -L'$_1$-C(R'$_2$)('R$_3$)—C(=Y'$_1$) include:

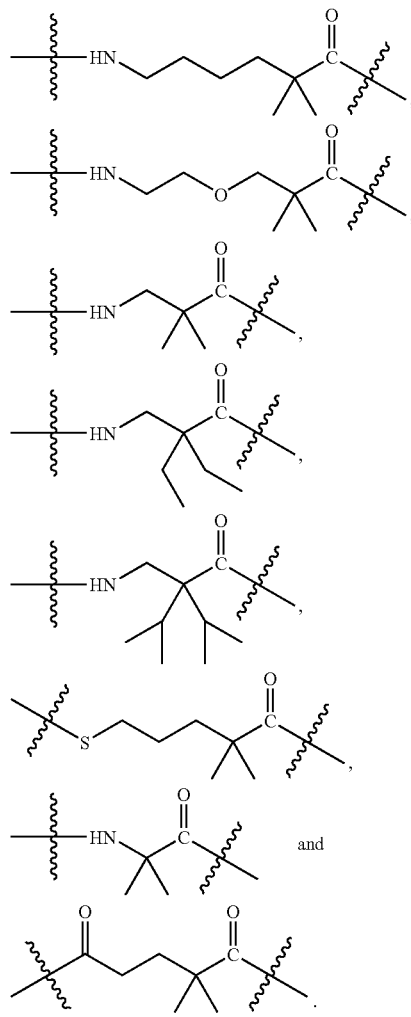

In another aspect, the polymeric delivery systems described herein include that R$_3$ is a substituted or unsubstituted hydrocarbon having at least three carbons when R$_2$ is H, and L$_1$ is not the same as C(R$_2$)(R$_3$).

E. Bifunctional Linkers

The compounds described herein can include bifunctional linkers. The bifunctional linkers include amino acids or amino acid derivatives. The amino acids can be among naturally occurring and non-naturally occurring amino acids. Derivatives and analogs of the naturally occurring amino acids, as well as various art-known non-naturally occurring amino acids (D or L), hydrophobic or non-hydrophobic, are also contemplated to be within the scope of the invention. A suitable non-limiting list of the non-naturally occurring amino acids includes 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, N-ethylglycine, N-ethylasparagine, 3-hydroxyproline, 4-hydroxyproline, isodesmosine, allo-isoleucine, N-methylglycine, sarcosine, N-methyl-isoleucine, 6-N-methyl-lysine, N-methylvaline, norvaline, norleucine, and ornithine. Some preferred amino acid residues are selected from glycine, alanine, methionine and sarcosine, and more preferably, glycine.

Alternatively, L$_2$ and L'$_2$ can be selected from among:
—[C(=O)]$_v$(CR$_{22}$R$_{23}$)$_t$[C(=O)]$_{v'}$—,
—[C(=O)]$_v$(CR$_{23}$R$_{23}$)$_t$—O[C(=O)]$_{v'}$—,
—[C(=O)]$_v$(CR$_{22}$R$_{23}$)$_t$—NR$_{26}$[C(=O)]$_{v'}$—,
—[C(=O)]$_v$O(CR$_{22}$R$_{23}$)$_t$[C(=O)]$_{v'}$—,
—[C(=O)]$_v$O(CR$_{22}$R$_{23}$)$_t$O[C(=O)]$_{v'}$—,
—[C(=O)]$_v$O(CR$_{22}$R$_{23}$)$_t$NR$_{26}$[C(=O)]$_{v'}$—,
—[C(=O)]$_v$NR$_{21}$(CR$_{22}$R$_{23}$)$_t$[C(=O)]$_{v'}$—,
—[C(=O)]$_v$NR$_{21}$(CR$_{22}$R$_{23}$)$_t$O[C(=O)]$_{v'}$—,
—[C(=O)]$_v$NR$_{21}$(CR$_{22}$R$_{23}$)$_t$NR$_{26}$[C(=O)]$_{v'}$—,
—[C(=O)]$_v$(CR$_{22}$R$_{23}$)$_t$O—(CR$_{28}$R$_{29}$)$_{t'}$[C(=O)]$_{v'}$—,
—[C(=O)]$_v$(CR$_{22}$R$_{23}$)$_t$NR$_{26}$—(CR$_{28}$R$_{29}$)$_{t'}$[C(=O)]$_{v'}$—,
—[C(=O)]$_v$(CR$_{22}$R$_{23}$)$_t$S—(CR$_{28}$R$_{29}$)$_{t'}$[C(=O)]$_{v'}$—,
—[C(=O)]$_v$O(CR$_{22}$R$_{23}$)$_t$O—(CR$_{28}$R$_{29}$)$_{t'}$[C(=O)]$_{v'}$—,
—[C(=O)]$_v$O(CR$_{22}$R$_{23}$)$_t$NR$_{26}$—(CR$_{28}$R$_{29}$)$_{t'}$[C(=O)]$_{v'}$—,
—[C(=O)]$_v$O(CR$_{22}$R$_{23}$)$_t$S—(CR$_{28}$R$_{29}$)$_{t'}$[C(=O)]$_{v'}$—,
—[C(=O)]$_v$NR$_{21}$(CR$_{22}$R$_{23}$)$_t$O—(CR$_{28}$R$_{29}$)$_{t'}$[C(=O)]$_{v'}$—,
—[C(=O)]$_v$NR$_{21}$(CR$_{22}$R$_{23}$)$_t$NR$_{26}$—(CR$_{28}$R$_{29}$)$_{t'}$[C(=O)]$_{v'}$—,
—[C(=O)]$_v$NR$_{21}$(CR$_{22}$R$_{23}$)$_t$S—(CR$_{28}$R$_{29}$)$_{t'}$[C(=O)]$_{v'}$—,
—[C(=O)]$_v$(CR$_{22}$R$_{23}$CR$_{28}$R$_{29}$O)$_t$NR$_{26}$[C(=O)]$_{v'}$—,
—[C(=O)]$_v$(CR$_{22}$R$_{23}$CR$_{28}$R$_{29}$O)$_t$[C(=O)]$_{v'}$—,
—[C(=O)]$_v$O(CR$_{22}$R$_{23}$CR$_{28}$R$_{29}$O)$_t$NR$_{26}$[C(=O)]$_{v'}$—,
—[C(=O)]$_v$O(CR$_{22}$R$_{23}$CR$_{28}$R$_{29}$O)$_t$[C(=O)]$_{v'}$—,
—[C(=O)]$_v$NR$_{21}$(CR$_{22}$R$_{23}$CR$_{28}$R$_{29}$O)$_t$NR$_{26}$[C(=O)]$_{v'}$—,
—[C(=O)]$_v$NR$_{21}$(CR$_{22}$R$_{23}$CR$_{28}$R$_{29}$O)$_t$[C(=O)]$_{v'}$—,
—[C(=O)]$_v$(CR$_{22}$R$_{23}$CR$_{28}$R$_{29}$O)$_t$(CR$_{24}$R$_{25}$)$_{t'}$[C(=O)]$_{v'}$—,
—[C(=O)]$_v$O(CR$_{22}$R$_{23}$CR$_{28}$R$_{29}$O)$_t$(CR$_{24}$R$_{25}$)$_{t'}$[C(=O)]$_{v'}$—,
—[C(=O)]$_v$NR$_{21}$(CR$_{22}$R$_{23}$CR$_{28}$R$_{29}$O)$_t$(CR$_{24}$R$_{25}$)$_{t'}$[C(=O)]$_{v'}$—,
—[C(=O)]$_v$(CR$_{22}$R$_{23}$CR$_{28}$R$_{29}$O)$_t$(CR$_{24}$R$_{25}$)$_{t'}$O[C(=O)]$_{v'}$—,
—[C(=O)]$_v$(CR$_{22}$R$_{23}$)$_t$(CR$_{24}$R$_{25}$CR$_{28}$R$_{29}$O)$_{t'}$[C(=O)]$_{v'}$—, —[C(=O)]$_v$(CR$_{22}$R$_{23}$)$_t$(CR$_{24}$R$_{25}$CR$_{28}$R$_{29}$O)$_t$NR$_{26}$[C(=O)]$_{v'}$—, —[C(=O)]$_v$O(CR$_{22}$R$_{23}$CR$_{28}$R$_{29}$O)$_t$(CR$_{24}$R$_{25}$)$_t$O[C(=O)]$_{v'}$—, —[C(=O)]$_v$O(CR$_{22}$R$_{23}$)$_t$(CR$_{24}$R$_{25}$CR$_{28}$R$_{29}$O)$_{t'}$[C(=O)]$_{v'}$—, —[C(=O)]$_v$O(CR$_{22}$R$_{23}$)$_t$(CR$_{24}$CR$_{25}$CR$_{28}$R$_{29}$O)$_t$NR$_{26}$[C(=O)]$_{v'}$—, —[C(=O)]$_v$NR$_{21}$(CR$_{22}$R$_{23}$CR$_{28}$R$_{29}$O)$_t$(CR$_{24}$R$_{25}$)$_t$O[C(=O)]$_{v'}$—, —[C(=O)]$_v$NR$_{21}$(CR$_{22}$R$_{23}$)$_t$(CR$_{24}$R$_{25}$CR$_{28}$R$_{29}$O)$_t$[C(=O)]$_{v'}$—, —[C(=O)]$_v$NR$_{21}$(CR$_{22}$R$_{23}$)$_t$(CR$_{24}$R$_{25}$CR$_{28}$R$_{29}$O)$_t$NR$_{26}$[C(=O)]$_{v'}$—,

[structures: N-methyl-4-methylpiperidine-2,6-dione; N-methyl-aminoethyl-3-methylsuccinimide]

—[C(=O)]$_v$O(CR$_{22}$R$_{23}$)$_t$—[phenyl with R$_{27}$]—(CR$_{24}$R$_{25}$)$_t$NR$_{26}$[C(=O)]$_{v'}$—, —[C(=O)]$_v$O(CR$_{22}$R$_{23}$)$_t$—[phenyl with R$_{27}$]—(CR$_{24}$R$_{25}$)$_t$O[C(=O)]$_{v'}$—, —[C(=O)]$_v$NR$_{21}$(CR$_{22}$R$_{23}$)$_t$—[phenyl with R$_{27}$]—(CR$_{24}$R$_{25}$)$_t$NR$_{26}$[C(=O)]$_{v'}$— and

—[C(=O)]$_v$NR$_{21}$(CR$_{22}$R$_{23}$)$_t$—[phenyl with R$_{27}$]—(CR$_{24}$R$_{25}$)$_t$O[C(=O)]$_{v'}$—, wherein:

R$_{21-29}$ are independently selected from the group consisting of hydrogen, C$_{1-6}$ alkyls, C$_{3-12}$ branched alkyls, C$_{3-8}$ cycloalkyls, C$_{1-6}$ substituted alkyls, C$_{3-8}$ substituted cyloalkyls, aryls, substituted aryls, aralkyls, C$_{1-6}$ heteroalkyls, substituted C$_{1-6}$ heteroalkyls, C$_{1-6}$ alkoxy, phenoxy and C$_{1-6}$ heteroalkoxy;

(t) and (t') are independently zero or a positive integer, preferably zero or an integer from about 1 to about 12, more preferably an integer from about 1 to about 8, and most preferably 1 or 2; and (v) and (v') are independently zero or 1.

In a preferred embodiment, L$_2$ and L'$_2$ can be selected from among:

—[C(=O)]$_r$NH(CH$_2$)$_2$CH=N—NHC(=O)—(CH$_2$)$_2$—,

—[C(=O)]$_r$NH(CH$_2$)$_2$(CH$_2$CH$_2$O)$_2$(CH$_2$)$_2$NH[C(=O)]$_{r'}$—,

—[C(=O)]$_r$NH(CH$_2$CH$_2$)(CH$_2$CH$_2$O)$_2$NH[C(=O)]$_{r'}$—,

—[C(=O)]$_r$NH(CH$_2$CH$_2$)$_s$NH(CH$_2$CH$_2$)$_s$[C(=O)]$_{r'}$—,

—[C(=O)]$_r$NH(CH$_2$CH$_2$)$_s$S(CH$_2$CH$_2$)$_s$[C(=O)]$_{r'}$—,

—[C(=O)]$_r$NH(CH$_2$CH$_2$)(CH$_2$CH$_2$O)[C(=O)]$_{r'}$—,

—[C(=O)]$_r$NH(CH$_2$CH$_2$)$_s$O(CH$_2$CH$_2$)$_s$[C(=O)]$_{r'}$—,

—[C(=O)]$_r$NH(CH$_2$CH$_2$O)(CH$_2$)NH[C(=O)]$_{r'}$—,

—[C(=O)]$_r$NH(CH$_2$CH$_2$O)$_2$(CH$_2$)[C(=O)]$_{r'}$—,

—[C(=O)]$_r$NH(CH$_2$CH$_2$O)$_s$[C(=O)]$_{r'}$—,

—[C(=O)]$_r$NHCH$_2$CH$_2$NH[C(=O)]$_{r'}$—,

—[C(=O)]$_r$NH(CH$_2$CH$_2$)$_2$O[C(=O)]$_{r'}$—,

—[C(=O)]$_r$NH(CH$_2$CH$_2$O)[C(=O)]$_{r'}$—,

—[C(=O)]$_r$NH(CH$_2$CH$_2$O)$_2$[C(=O)]$_{r'}$—,

—[C(=O)]$_r$NH(CH$_2$)$_3$[C(=O)]$_{r'}$—,

—[C(=O)]$_r$O(CH$_2$CH$_2$O)$_2$(CH$_2$)[C(=O)]$_{r'}$—,

—[C(=O)]$_r$O(CH$_2$)$_2$NH(CH$_2$)$_2$[C(=O)]$_{r'}$—,

—[C(=O)]$_r$O(CH$_2$CH$_2$O)$_2$NH[C(=O)]$_{r'}$—,

—[C(=O)]$_r$O(CH$_2$)$_2$O(CH$_2$)$_2$[C(=O)]$_{r'}$—,

—[C(=O)]$_r$O(CH$_2$)$_2$S(CH$_2$)$_2$[C(=O)]$_{r'}$—,

—[C(=O)]$_r$O(CH$_2$CH$_2$)NH[C(=O)]$_{r'}$—,

—[C(=O)]$_r$O(CH$_2$CH$_2$)O[C(=O)]$_{r'}$—,

—[C(=O)]$_r$O(CH$_2$)$_3$NH[C(=O)]$_{r'}$—,

—[C(=O)]$_r$O(CH$_2$)$_3$O[C(=O)]$_{r'}$—,

—[C(=O)]$_r$O(CH$_2$)$_3$[C(=O)]$_{r'}$—,

—[C(=O)]$_r$CH$_2$NHCH$_2$[C(=O)]$_{r'}$—,

—[C(=O)]$_r$CH$_2$OCH$_2$[C(=O)]$_{r'}$—,

—[C(=O)]$_r$CH$_2$SCH$_2$[C(=O)]$_{r'}$—,

—[C(=O)]$_r$CH$_2$)$_3$[C(=O)]$_{r'}$—,

—[C(=O)]$_r$OCH$_2$—[phenyl]—CH$_2$NH[C(=O)]$_{r'}$—,

—[C(=O)]$_r$OCH$_2$—[phenyl]—CH$_2$O[C(=O)]$_{r'}$—,

—[C(=O)]$_r$NHCH$_2$—[phenyl]—CH$_2$NH[C(=O)]$_{r'}$—, and

—[C(=O)]$_r$NHCH$_2$—[phenyl]—CH$_2$O[C(=O)]$_{r'}$— wherein (r) and (r') are independently zero or 1.

In yet another embodiment, the bifunctional linkers include:

[structure: $-\!\!-\!\![L_{11}]_{a11}[\overset{Y_{11}}{\underset{\|}{C}}]_{b11}Y_{12}-Ar-[\overset{R_{31}}{\underset{R_{32}}{C}}]_{c11}Y_{13}-\overset{Y_{14}}{\underset{\|}{C}}-\!\!\!-$ , $-\!\!-\!\![L_{12}]_{e11}[\overset{Y_{15}}{\underset{\|}{C}}]_{f11}O-[Ar(R_{37})]-[\overset{R_{33}}{\underset{R_{34}}{C}}]_{g11}[\overset{R_{35}}{\underset{R_{36}}{C}}]_{h11}\overset{Y_{16}}{\underset{\|}{C}}-\!\!\!-$,]

-continued

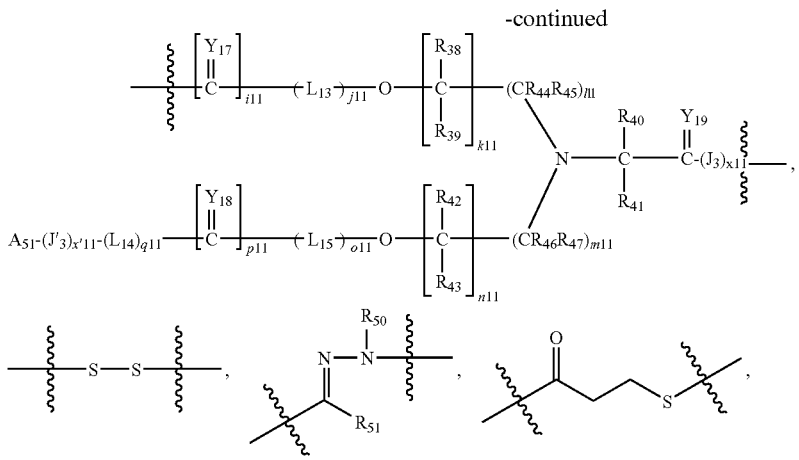

-Val-Cit-.
-Gly-Phe-Leu-Gly-,
-Ala-Leu-Ala-Leu-,
-Phe-Lys-,

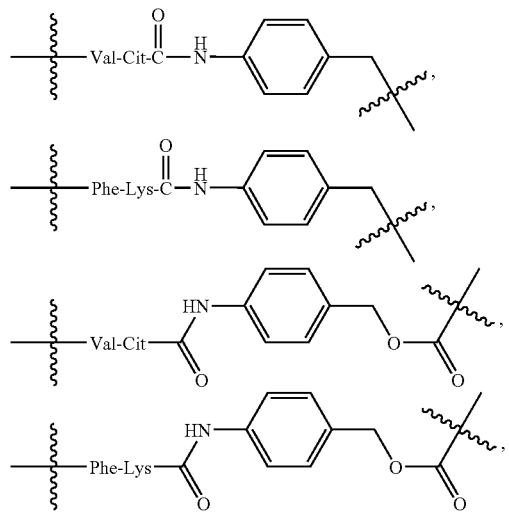

-Val-Cit-C(=O)—CH$_2$OCH$_2$—C(=O)—,
-Val-Cit-C(=O)—CH$_2$SCH$_2$—C(=O)—, and
—NHCH(CH$_3$)—C(=O)—NH(CH$_2$)$_6$—C(CH$_3$)$_2$—C(=O)— wherein, $Y_{11-19}$ are independently O, S or $NR_{48}$;

$R_{31-48}$, $R_{50-51}$ and $A_{51}$ are independently selected from the group consisting of hydrogen, $C_{1-6}$ alkyls, $C_{3-12}$ branched alkyls, $C_{3-8}$ cycloalkyls, substituted alkyls, $C_{3-8}$ substituted cyloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is an aryl or heteroaryl moiety;

$L_{11-15}$ are independently selected bifunctional spacers;

$J_3$ and $J'_3$ are independently selected from selected from among moieties actively transported into a target cell, hydrophobic moieties, bifunctional linking moieties and combinations thereof;

(c11), (h11), (k11), (l11), (m11) and (n11) are independently selected positive integers;

(a11), (e11), (g11), (j11), (o11) and (q11) are independently either zero or a positive integer; and (b11), (x11), (x'11), (f11), (i11) and (p11) are independently zero or one.

E. $R_4$ and $R'_4$ Groups

1. Leaving Groups

For purposes of the present invention, leaving groups are to be understood as those groups which are capable of reacting with a nucleophile found on the desired target, i.e. an oligonucleotide, a bifunctional spacer, intermediate, etc. The targets thus contain a group for displacement, such as OH or SH groups found on oligonucleotides.

Leaving groups attached to the hindered ester allows covalent reaction to the biologically active moiety of choice, i.e. pharmaceutically active compounds (small molecular weight compounds), oligonucleotides, etc. Suitable leaving groups include, without limitations, halogen (Br, Cl), activated esters, cyclic imide thione, N-hydroxysuccmimidyl, N-hydroxyphtalimidyl, N-hydroxybenzotriazolyl, imidazole, tosylate, mesylate, tresylate, nosylate, $C_1$-$C_6$ alkyloxy, $C_1$-$C_6$ alkanoyloxy, arylcarbonyloxy, ortho-nitrophenoxy, para-nitrophenoxy, pentafluorophenoxy, 1,3,5-trichlorophenoxy, and 1,3,5-trifluorophenoxy or other suitable leaving groups as will be apparent to those of ordinary skill.

In particularly preferred embodiments of the invention, the leaving groups can be selected from among OH, methoxy, tert-butoxy, para-nitrophenoxy and N-hydroxysuccinimidyl.

2. Polynucleotide Moieties

In order to more fully appreciate the scope of the present invention, the following terms are defined. The artisan will appreciate that the terms, "nucleic acid" or "nucleotide" apply to deoxyribonucleic acid ("DNA"), ribonucleic acid, ("RNA") whether single-stranded or double-stranded, unless otherwise specified, and any chemical modifications thereof. An "oligonucleotide" is generally a relatively short polynucleotide, e.g., ranging in size from about 2 to about 200 nucleotides, or more preferably from about 10 to about 30 nucleotides in length. The oligonucleotides according to the invention are generally synthetic nucleic acids, and are single stranded, unless otherwise specified. The terms, "polynucleotide" and "polynucleic acid" may also be used synonymously herein.

The term "antisense," as used herein, refers to nucleotide sequences which are complementary to a specific DNA or RNA sequence that encodes a gene product or that encodes a control sequence. The term "antisense strand" is used in reference to a nucleic acid strand that is complementary to the "sense" strand. In the normal operation of cellular metabolism, the sense strand of a DNA molecule is the strand that encodes polypeptides and/or other gene products. The sense strand serves as a template for synthesis of a messenger RNA ("mRNA") transcript (an antisense strand) which, in turn, directs synthesis of any encoded gene product. Antisense nucleic acid molecules may be produced by any art-known methods, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designations "negative" or (−) are also art-known to refer to the antisense strand, and "positive" or (+) are also art-known to refer to the sense strand.

For example, if it is intended to downregulate expression of an mRNA transcript in a cell or cells, the antisense oligonucleotide is introduced into a cell. Once introduced into a cell, the antisense oligonucleotide hybridizes to the corresponding mRNA sequence through Watson-Crick binding, forming a heteroduplex. Once the duplex is formed, translation of the protein coded by the sequence of bound mRNA is inhibited. Thus, antisense oligonucleotides are also employed in the art as probes, e.g., hybridization probes, generally linked to a tag or label, as well as being used to provide precise downregulation of the expression of specific cellular products or genetic regulatory elements for both investigational and therapeutic purposes.

A wide variety of polynucleotide moieties can be attached to the activated polymers described herein.

In one aspect of the invention, the polynucleotides are suitable for medicinal or diagnostic use in the treatment of animals, e.g., mammals, including humans, for conditions for which such treatment is desired.

In yet another aspect, hydroxyl- or thiol-containing polynucleotides are within the scope of the present invention. The only limitations on the types of the biologically active moieties suitable for inclusion herein is that there is available at least one hydroxyl- or thiol-group which can react and link with a carrier portion and that there is not substantial loss of bioactivity in the form of conjugated to the polymeric delivery systems described herein.

Alternatively, parent compounds suitable for incorporation into the polymeric transport conjugate compounds of the invention, maybe active after hydrolytic release from the linked compound, or not active after hydrolytic release but which will become active after undergoing a further chemical process/reaction. For example, an anticancer drug that is delivered to the bloodstream by the polymeric transport system, may remain inactive until entering a cancer or tumor cell, whereupon it is activated by the cancer or tumor cell chemistry, e.g., by an enzymatic reaction unique to that cell.

In one preferred embodiment, the choice for conjugation is an oligonucleotide and after conjugation, the target is referred to as a residue of an oligonucleotide. The oligonucleotides can be selected from among any of the known oligonucleotides and oligodeoxynucleotides with phosphorodiester backbones or phosphorothioate backbones, locked nucleic acid(LNA), nucleic acid with peptide backbone(PNA), tricyclo-DNA, double stranded oligonucleotide (decoy ODN), catalytic RNA sequence (RNAi), ribozymes, spiegelmers, and CpG oligomers. Those of ordinary skill in the art will further realize that the foregoing list is merely illustrative and that all nucleic acid materials are contemplated.

Preferably, the polynucleotides include 2 to 100 oligomer oligonucleotides, more preferably 3 to 50 oligomers and most preferably 10 to 30 oligomers. All other suitable size of the oligonucleotides is also contemplated.

The polynucleotides of the compounds described herein can be single stranded or double stranded including phosphorodiester backbone or phosphorothioate backbone. The "polynucleotide" (or "oligonucleotide") includes oligonucleotides and oligodeoxynucleotides, including, for example, an oligonucleotide that has the same or substantially similar nucleotide sequence as does Genasense (a/k/a oblimersen sodium, produced by Genta Inc., Berkeley Heights, N.J.). Genasense is an 18-mer phosphorothioate antisense oligonucleotide, TCTCCCAGCGTGCGCCAT (SEQ ID NO: 4), that is complementary to the first six codons of the initiating sequence of the human bcl-2 mRNA (human bcl-2 mRNA is art-known, and is described, e.g., as SEQ ID NO: 19 in U.S. Pat. No. 6,414,134, incorporated by reference herein). The U.S. Food and Drug Administration (FDA) gave Genasense Orphan Drug status in August 2000.

Further, oligonucleotides and oligodeoxynucleotides useful according to the invention include, but are not limited to, the following:

Oligonucleotides and oligodeoxynucleotides with natural phosphorodiester backbone or phosphorothioate backbone or any other modified backbone analogues;

LNA (Locked Nucleic Acid);
PNA (nucleic acid with peptide backbone);
tricyclo-DNA;
decoy ODN (double stranded oligonucleotide);
catalytic RNA sequence;
ribozymes;
spiegelmers (L-conformational oligonucleotides);
CpG oligomers, and the like, such as those disclosed at:
Tides 2002, Oligonucleotide and Peptide Technology Conferences, May 6-8, 2002, Las Vegas, Nev. and Oligonucleotide & Peptide Technologies, 18th & 19th Nov. 2003, Hamburg, Germany, the contents of which are incorporated herein by reference.

Oligonucleotides according to the invention can also optionally include any suitable art-known nucleotide analogs and derivatives, including those listed by Table 1, below:

TABLE 1

Representative Nucleotide Analogs And Derivatives

| | |
|---|---|
| 4-acetylcytidine | 5-methoxyaminomethyl-2-thiouridine |
| 5-(carboxyhydroxymethyl)uridine | beta, D-mannosylqueuosine |
| 2'-O-methylcytidine | 5-methoxycarbonylmethyl-2-thiouridine |
| 5-carboxymethylaminomethyl-2-thiouridine | 5-methoxycarbonylmethyluridine |
| 5-carboxymethylaminomethyluridine | 5-methoxyuridine |
| Dihydrouridine | 2-methylthio-N6-isopentenyladenosine |
| 2'-O-methylpseudouridine | N-((9-beta-D-ribofuranosyl-2-methylthiopurine-6-yl)carbamoyl)threonine |
| D-galactosylqueuosine | N-((9-beta-D-ribofuranosylpurine-6-yl)N-methylcarbamoyl)threonine |
| 2'-O-methylguanosine | uridine-5-oxyacetic acid-methylester |
| Inosine | uridine-5-oxyacetic acid |
| N6-isopentenyladenosine | wybutoxosine |
| 1-methyladenosine | pseudouridine |
| 1-methylpseudouridine | queuosine |
| 1-methylguanosine | 2-thiocytidine |
| 1-methylinosine | 5-methyl-2-thiouridine |

TABLE 1-continued

Representative Nucleotide Analogs And Derivatives

| | |
|---|---|
| 2,2-dimethylguanosine | 2-thiouridine |
| 2-methyladenosine | 4-thiouridine |
| 2-methylguanosine | 5-methyluridine |
| 3-methylcytidine | N-((9-beta-D-ribofuranosylpurine-6-yl)-carbamoyl)threonine |
| 5-methylcytidine | 2'-O-methyl-5-methyluridine |
| N6-methyladenosine | 2'-O-methyluridine |
| 7-methylguanosine | wybutosine |
| 5-methylaminomethyluridine | 3-(3-amino-3-carboxy-propyl)uridine |
| locked adenine | locked cytosine |
| locked guanine | locked thymine |
| locked uridine | locked methyl cytosine |

Modifications to the oligonucleotides contemplated in the invention include, for example, the addition to or substitution of selected nucleotides with functional groups or moieties that permit covalent linkage of an oligonucleotide to a desirable polymer, and/or the addition or substitution of functional moieties that incorporate additional charge, polarizability, hydrogen bonding, electrostatic interaction, and functionality to an oligonucleotide. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodouracil, backbone modifications, methylations, base-pairing combinations such as the isobases isocytidine and isoguanidine, and analogous combinations. Oligonucleotide modifications can also include 3' and 5' modifications such as capping. Structures of illustrative nucleoside analogs are provided below.

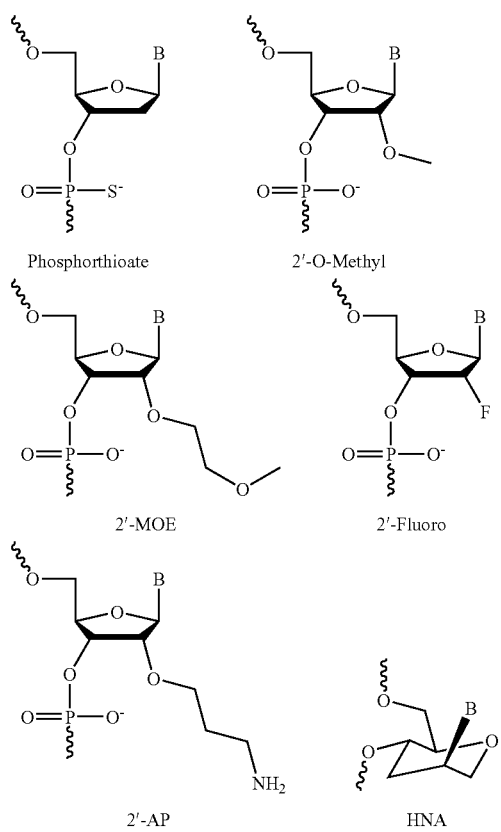

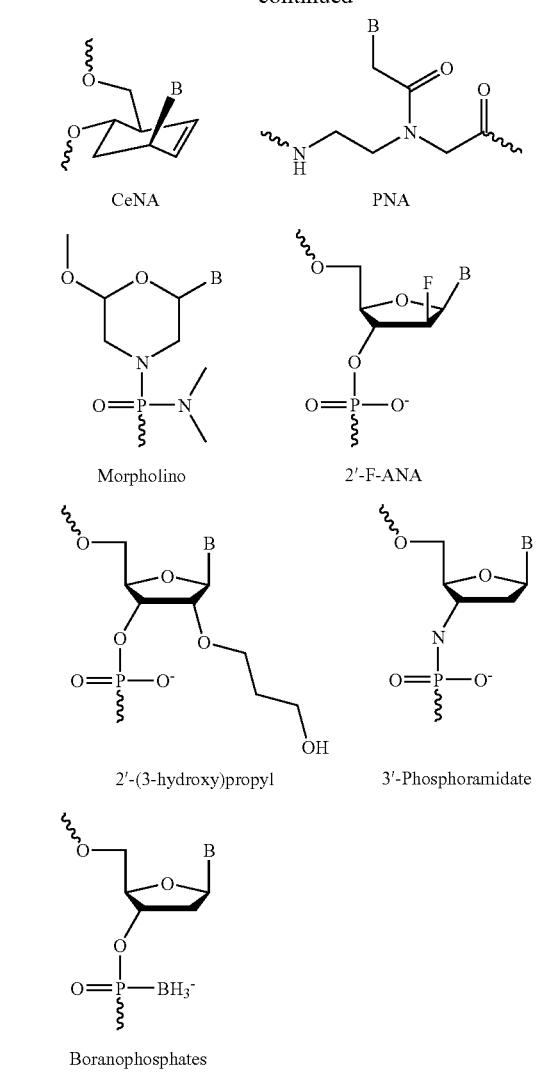

See more examples of nucleoside analogues described in Freier & Altmann; Nucl. Acid Res., 1997, 25, 4429-4443 and Uhlmann; Curr. Opinion in Drug Development, 2000, 3(2), 293-213, the contents of each of which are incorporated herein by reference.

Although antisense oligonucleotides and related compounds have been mentioned as preferred targets for the attachment of the polymers containing the hindered esters, it is intended that $R_4$ or $R'_4$ include all suitable polynucleotides known to benefit from PEG or polymer attachment.

Preferably, the oligonucleotide is involved in targeted tumor cells or downregulating a protein implicated in the resistance of tumor cells to anticancer therapeutics. For example, any art-known cellular proteins such as BCL-2 for downregulation by antisense oligonucleotides, for cancer therapy, can be used for the present invention. See U.S. patent application Ser. No. 10/822,205 filed Apr. 9, 2004, the contents of which are incorporated by reference herein. A non-limiting list of preferred therapeutic oligonucleotides includes antisense HIF-1a oligonucleotides and antisense Survivin oligonucleotides.

Preferred embodiments include:

(i) antisense Survivin LNA
(SEQ ID NO: 1)
$^mC_s$-$T_s$-$^mC_s$-$A_s$-$a_s$-$t_s$-$c_s$-$c_s$-$a_s$-$t_s$-$g_s$-$g_s$-$^mC_s$-$A_s$-$G_s$-c;

where the upper case letter represents LNA, the "s" represents a phosphorothioate backbone;

(ii) antisense Bcl2 siRNA:
(SEQ ID NO: 2)
SENSE  5'- GCAUGCGGCCUCUGUUUGAdTdT-3'

(SEQ ID NO: 3)
ANTISENSE  3'- dTdTCGUACGCCGGAGACAAACU-5' where dT represents DNA;

(iii) Genasense (phosphorothioate antisense oligonucleotide):
$t_s$-$c_s$-$t_s$-$c_s$-$c_s$-$c_s$-$a_s$-$g_s$-$c_s$-$g_s$-$t_s$-$g_s$-$c_s$-$g_s$-$c_s$-$c_s$-$c_s$-$a_s$-t
(SEQ ID NO: 4)

where the lower case letter represents DNA and and "s" represents phosphorothioate backbone;

(iv) antisense HIF1α LNA
(SEQ ID NO: 5)
5'-$_s$$T_s$$G_s$$G_s$$c_s$$a_s$$a_s$$g_s$$c_s$$a_s$$t_s$$c_s$$c_s$$T_s$$G_s$$T_s$a-3' where the upper case letter represents LNA and the "s" represents phosphorothioate backbone.

LNA includes 2'-O,4'-C methylene bicyclonucleotide as shown below:

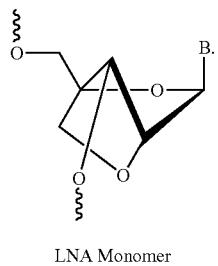

LNA Monomer
β-D configuration

See Detailed description of Survivin LNA disclosed in U.S. patent application Ser. No. 11/272,124, entitled "LNA Oligonucleotides and the Treatment of Cancer" and Ser. No. 10/776,934, entitled "Oligomeric Compounds for the Modulation Survivin Expression", the contents of each of which are incorporated herein by reference. See also U.S. patent application Ser. No. 10/407,807, entitled "Oligomeric Compounds for the Modulation HIF-1 Alpha Expression" and Ser. No. 11/271,686, entitled "Potent LNA Oligonucleotides for Inhibition of HIF-1A Expression", the contents of which are also incorporated herein by reference.

In one preferred embodiment, the compounds described herein can include oligonucleotides modified with hindered ester-containing $(CH_2)_w$ amino linkers at 5' or 3' end of the oligonucleotides, where w in this aspect is a positive integer of preferably from about 1 to about 10, preferably about 6. The polymeric compounds can release the oligonucleotides without amino tail. For example, the oligonucleotides can have the structure:

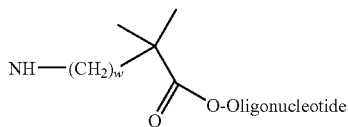

wherein w is a positive integer from about 1 to about 10, preferably about 6.

In yet another preferred embodiment, oligonucleotides can include $(CH_2)_w$ sulfhydryl linkers (thio oligonucleotides). The thio oligonucletides can be used for conjugating directly to cysteine of the positively charge peptide or via maleimidyl group. The thio oligonucleotides can have the structure:

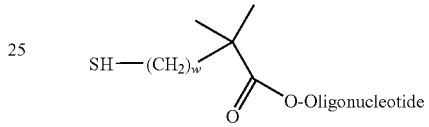

A further aspect of the invention provides the conjugate compounds optionally prepared with a diagnostic tag linked to the polymeric delivery system described herein, wherein the tag is selected for diagnostic or imaging purposes. Thus, a suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In yet a further aspect of the invention, the inventive tagged conjugates are readily prepared, by art-known methods, with any suitable label, including, e.g., radioisotope labels. Simply by way of example, these include [131]Iodine, [125]Iodine, [99m]Technetium and/or [111]Indium to produce radioimmunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888,474; 5,997,844; and 5,997,845, incorporated by reference herein.

F. Preferred Embodiments Corresponding to Formula (I)

The compound according to Formula (I) is covalently conjugated to a substantially nonantigenic polymer, e.g., a polyalkylene oxide. In particular preferred embodiments, the compound according to Formula (I) includes the following:

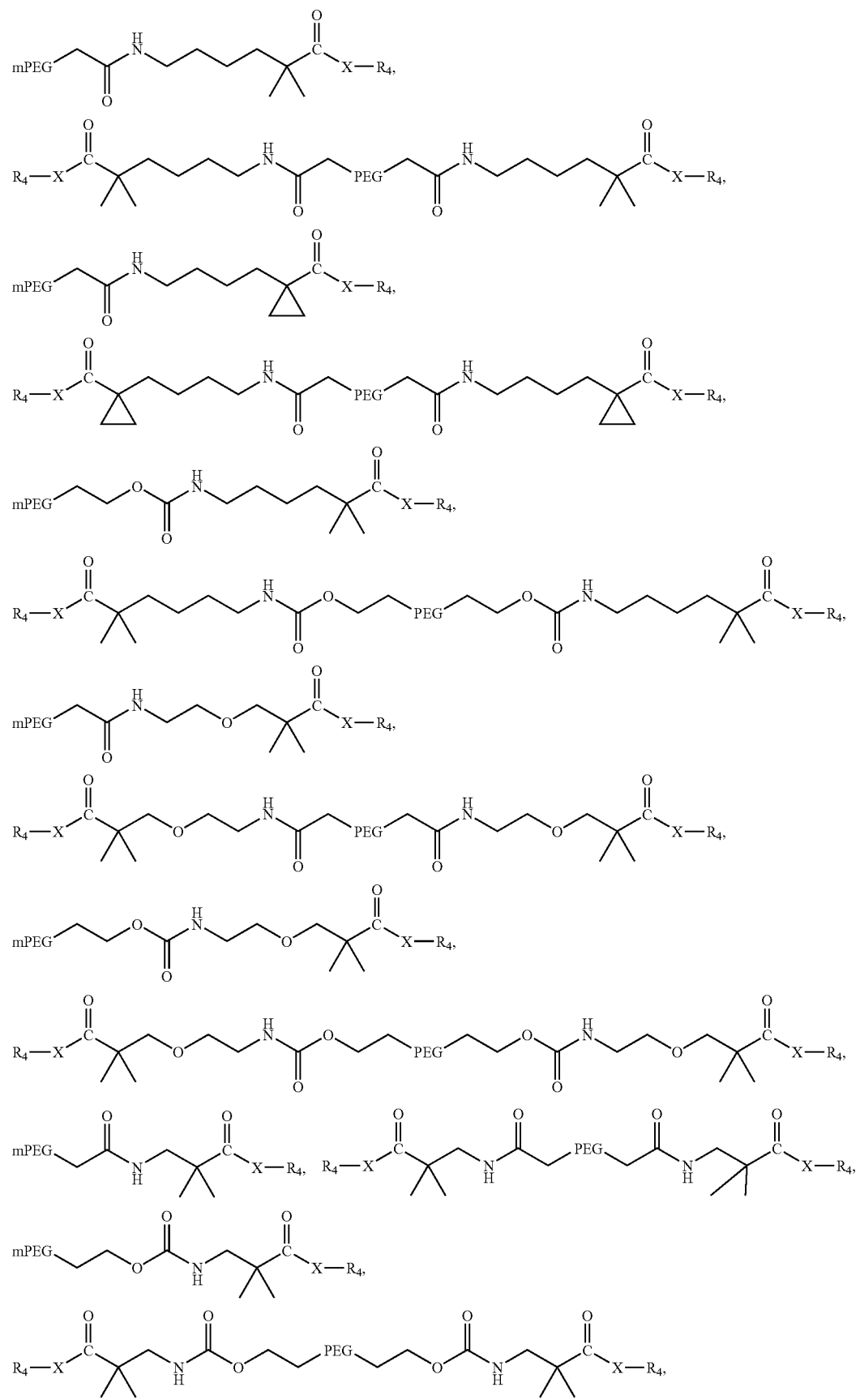

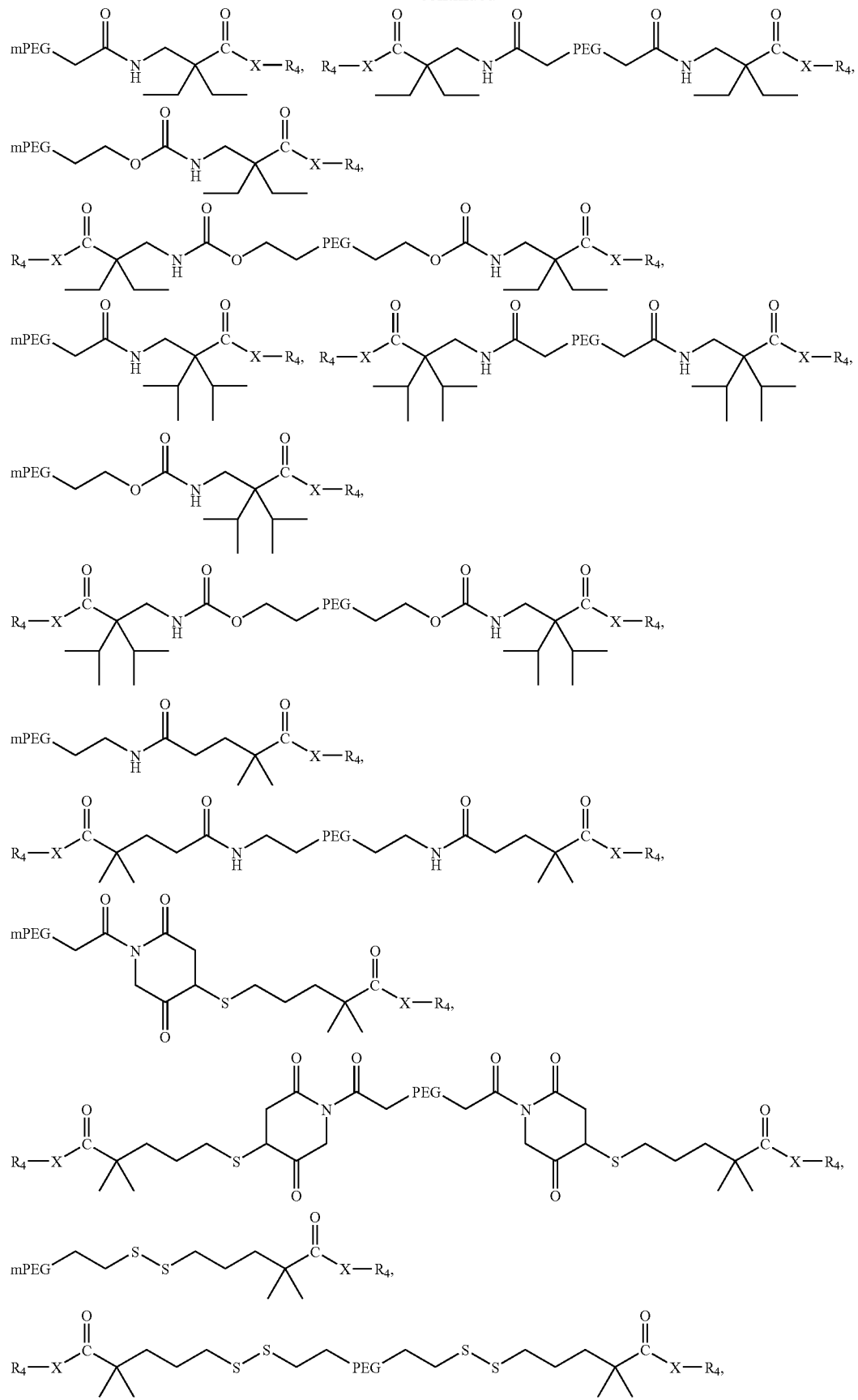

-continued
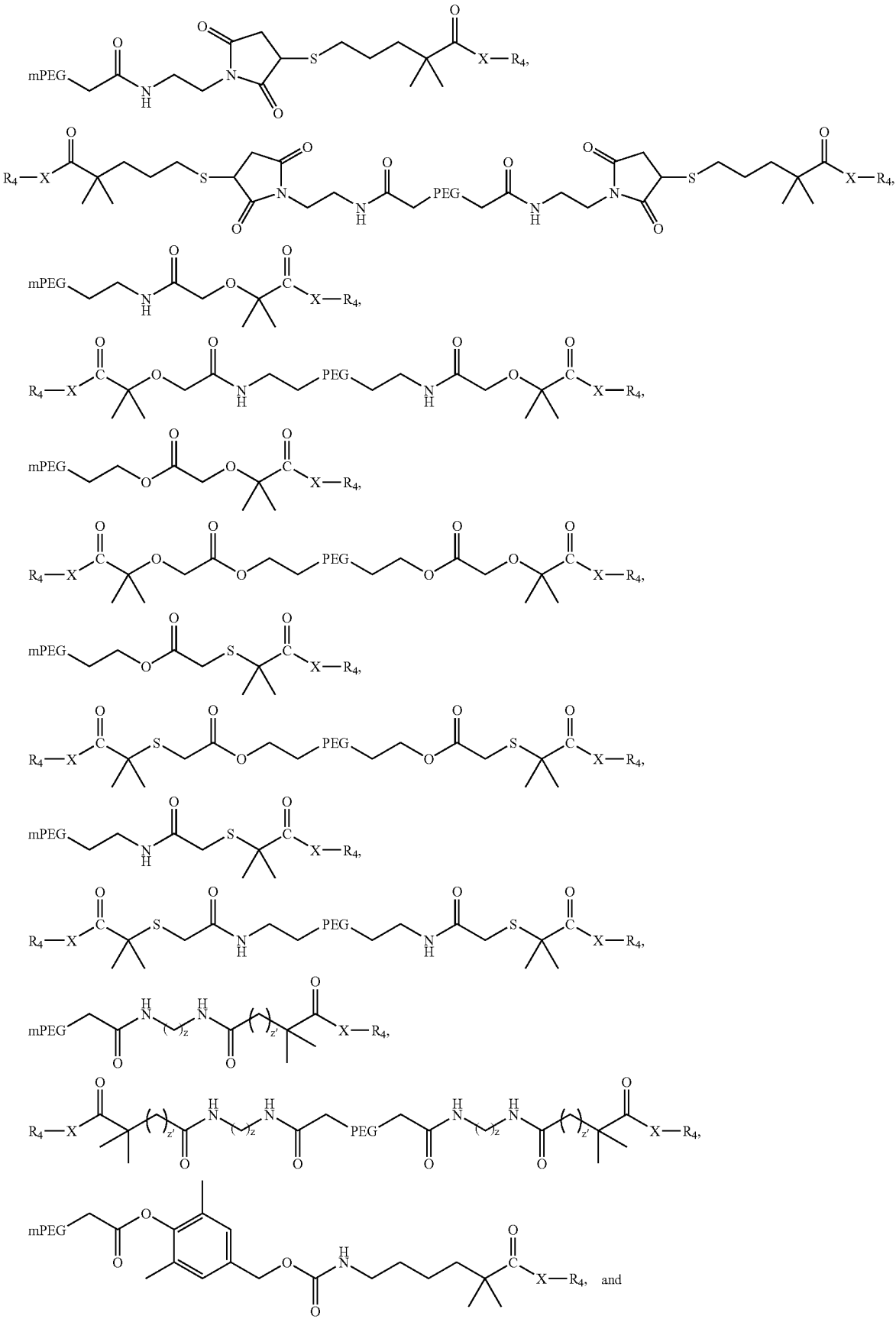

-continued

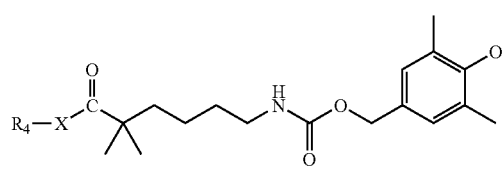 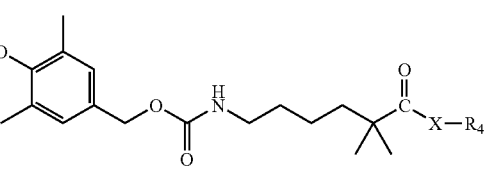

wherein:

$R_4$ is selected from among sense oligonucleotides, antisense oligonucleotides, locked nucleic acids (LNA), short interfering RNA (siRNA), microRNA (miRNA), aptamers, peptide nucleic acid (PNA), phosphorodiamidate morpholino oligonucleotides (PMO), tricyclo-DNA, double stranded oligonucleotide (decoy ODN), catalytic RNA (RNAi), aptamers, spiegelmers, CpG oligomers and in combination;

(z) is a positive integer from about 1 to about 10;
(z') is zero or a positive integer from about 1 to about 4;
mPEG has the formula: $CH_3—O(CH_2CH_2O)_n—$;
PEG has the formula $—O(CH_2CH_2O)_n—$; and
(n) is a positive integer from about 10 to about 2,300.

Preferred polymeric compounds according to the present invention include:

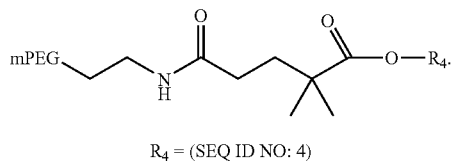

$R_4$ = (SEQ ID NO: 4)

One preferred embodiment for $R_4$ includes:

(i) antisense Survivin LNA
                                    (SEQ ID NO: 1)
$^mC_s$-$T_s$-$^mC_s$-$A_s$-$a_s$-$t_s$-$c_s$-$c_s$-$a_s$-$t_s$-$g_s$-$g_s$-$^mC_s$-$A_s$-$G_s$-c;

where the upper case letter represents LNA, the "s" represents a phosphorothioate backbone;

(ii) antisense Bcl2 siRNA:
                                    (SEQ ID NO: 2)
SENSE      5'- GCAUGCGGCCUCUGUUUGAdTdT-3'

(SEQ ID NO: 3)
ANTISENSE  3'- dTdTCGUACGCCGGAGACAAACU-5' where dT represents DNA;

(iii) Genasense (phosphorothioate antisense oligonucleotide):
$t_s$-$c_s$-$t_s$-$c_s$-$c_s$-$c_s$-$a_s$-$g_s$-$c_s$-$g_s$-$t_s$-$g_s$-$c_s$-$g_s$-$c_s$-$c_s$-$c_s$-$a_s$-t where the lower case letter represents DNA and and "s" represents phosphorothioate backbone;

(iv) antisense HIF1α LNA
                                    (SEQ ID NO: 5)
5'-$_s$T$_s$G$_s$G$_s$c$_s$a$_s$a$_s$g$_s$c$_s$a$_s$t$_s$c$_s$c$_s$T$_s$G$_s$T$_s$a-3' where the upper case letter represents LNA and the "s" represents phosphorothioate backbone.

For purposes of the present invention, Genasense (SEQ ID NO: 4) is described as TCTCCCAGCGTGCGCCAT or 5'-$t_s$c$_s$t$_s$c$_s$c$_s$c$_s$a$_s$g$_s$c$_s$g$_s$t$_s$g$_s$c$_s$g$_s$c$_s$c$_s$a$_s$t-3'.

G. Methods of Making the Conjugates

In one aspect of the invention, the polymeric compound having hindered ester can be prepared by conjugating a polymeric compound having an OH or a leaving group at the terminal end with a nucleophile having a protected hindered ester or a hindered acid at the distal end. Further deprotecting and activating the resulting polymeric compound will provide the compound of the current invention. The terminal group of the current invention can be either carboxylic acid form ready to be coupled with OH or SH containing moiety or an activated form which can be replaced upon conjugating with OH or SH containing moiety.

Alternatively, OH or SH containing compound can be conjugated to form a hindered ester intermediate, which in turn reacted with an activated polymer for the polymeric conjugate having a hindered ester with a biologically active moiety.

For purposes of illustration, the methods of preparing a hindered acyl or ester moiety-containing polymeric conjugate include:

reacting a compound of Formula (III):

$$A_1-R_1-M_1 \quad (III)$$

with a compound of Formula (IV)

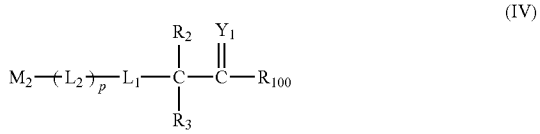 (IV)

under conditions sufficient to form a compound of Formula (V):

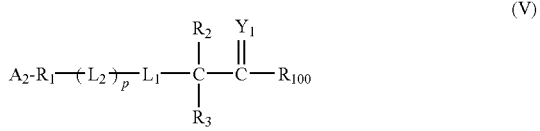 (V)

wherein:

$A_1$ is a capping group or $M_1$;
$A_2$ is a capping group or

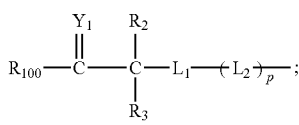

$M_1$ is a leaving group such as halogens, activated carbonates, isocyanate, N-hydroxysuccinimidyl, tosylate, mesylate, tresylate, nosylate, ortho-nitrophenoxy, imidazole and other leaving groups known by those of ordinary skill in the art;

$M_2$ is —OH, —SH, or —NHR$_{101}$;

$R_{100}$ is OH or OR$_{101}$; wherein, R$_{101}$ is selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted aryloxycarbonyloxy; and all other variables are as previously defined.

The attachment of the hindered ester moiety according to Formula (IV) to the PEG or other polymer can be done using standard chemical synthetic techniques well known to those of ordinary skill. The activated polymer portion such as SC-PEG, PEG-amine, PEG acids, etc. can be obtained from either commercial sources or synthesized by the artisan without undue experimentation.

For the purpose of the current invention, a non-limiting list of such hindered ester moiety includes:

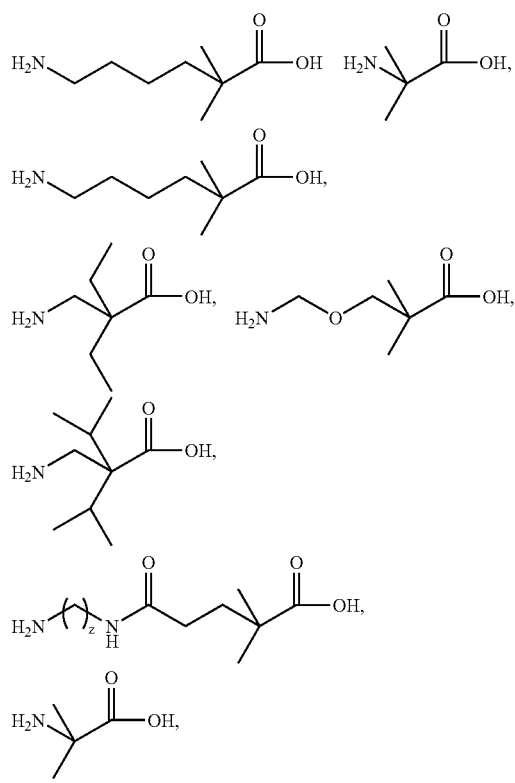

wherein, (z) is as previously defined.

The compounds of Formula (V) can further react with a —OH or —SH containing moiety in the presence of base and a coupling agent under conditions sufficient to form a compound of Formula (Ia):

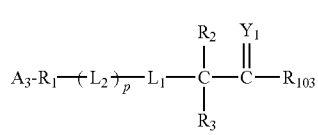

(Ia)

wherein:

A$_3$ is a capping group or

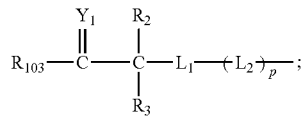

and

R$_{103}$ is selected from among targeting agents, diagnostic agents and biologically active moieties; and all other variables are previously defined.

For purposes of the present invention, the R$_{103}$ shall be understood as the portion of the OH or SH containing moiety which remains after it has undergone a reaction with the compound of Formula (V).

Alternatively, the compounds described herein can be prepared by methods including:

reacting a compound of Formula (VI):

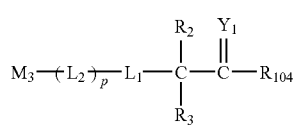

(VI)

with a compound of Formula (VII):

$$A_4\text{-}R_1\text{-}M_4 \quad \text{(VII)}$$

under conditions sufficient to form a compound of Formula (VIII):

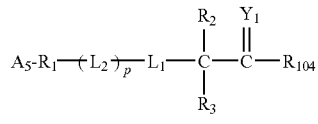

(VIII)

herein:

$A_4$ is a capping group or $M_4$;

$A_5$ is a capping group or

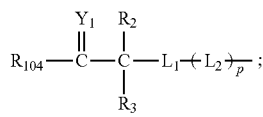

$M_3$ is —OH, SH, or —$NHR_{105}$;

$M_4$ is a leaving group such as halogens, activated carbonates, isocyanate, N-hydroxysuccmimidyl, tosylate, mesylate, tresylate, nosylate, ortho-nitrophenoxy, imidazole and other leaving groups known by those of ordinary skill in the art;

$R_{104}$ iselected from biologically active moieties, targeting groups and diagnostic agents $R_{105}$ is selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-6}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, $C_{2-6}$ substituted aryloxycarbonyl, $C_{2-6}$ substituted alkanoyloxy and substituted arylcarbonyloxy; and all other variables are previously defined.

Attachment of the hindered ester containing group to the polymer portion is preferably carried out in the presence of a coupling agent. A non-limiting list of suitable coupling agents include 1,3-diisopropylcarbodiimide (DIPC), any suitable dialkyl carbodiimides, 2-halo-1-alkyl-pyridinium halides, (Mukaiyama reagents), 1-(3-dimethylammopropyl)-3-ethyl carbodiimide (EDC), propane phosphonic acid cyclic anhydride (PPACA) and phenyl dichlorophosphates, etc. which are available, for example from commercial sources such as Sigma-Aldrich Chemical, or synthesized using known techniques.

Preferably, the reactions are carried out in an inert solvent such as methylene chloride, chloroform, DMF or mixtures thereof. The reactions can be preferably conducted in the presence of a base, such as dimethylaminopyridine (DMAP), diisopropylethylamine, pyridine, triethylamine, etc. to neutralize any acids generated. The reactions can be earned out at a temperature from about 0° C. up to about 22° C. (room temperature).

H. Methods of Treatment

Another aspect of the present invention provides methods of treatment for various medical conditions in mammals. The methods include administering, to the mammal in need of such treatment, an effective amount of a compound described herein. The polymeric conjugate compounds are useful for, among other things, treating diseases which are similar to those which are treated with the parent compound, e.g. enzyme replacement therapy, neoplastic disease, reducing tumor burden, preventing metastasis of neoplasms and preventing recurrences of tumor/neoplastic growths in mammals.

The amount of the polymeric conjugate that is administered will depend upon the amount of the parent molecule included therein. Generally, the amount of polymeric conjugate used in the treatment methods is that amount which effectively achieves the desired therapeutic result in mammals. Naturally, the dosages of the various polymeric conjugate compounds will vary somewhat depending upon the parent compound, molecular weight of the polymer, rate of in vivo hydrolysis, etc. Those skilled in the art will determine the optimal dosing of the polymeric transport conjugates selected based on clinical experience and the treatment indication. Actual dosages will be apparent to the artisan without undue experimentation.

The compounds of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, intraperitoneal, subcutaneous injection and the like. Such administration may also be by infusion into a body space or cavity, as well as by inhalation and/or intranasal routes. In preferred aspects of the invention, however, the polymeric conjugates are parenterally administered to mammals in need thereof.

In a further aspect of the invention, there are provided methods of administering polynucleotides (oligonucleotides), preferably antisense oligonucleotides to mammalian cells. The methods include delivering an effective amount of a conjugate prepared as described herein to the condition being treated will depend upon the polynucleotides efficacy for such conditions. For example, if the unconjugated oligonucleotides (for example antisense BCL2 oligonucleotides, antisense Survivin oligonucleotides) has efficacy against certain cancer or neoplastic cells, the method would include delivering a polymer conjugate containing the oligonucleotides to the cells having susceptibility to the native oligonucleotides. The delivery can be made in vivo as part of a suitable pharmaceutical composition or directly to the cells in an ex vivo environment. In one particular treatment, the polymeric conjugates including oligonucleotides (SEQ ID NO. 1, SEQ ID NOs: 2 and 3, and SEQ ID NO: 4) can be used.

EXAMPLES

Figure 2:
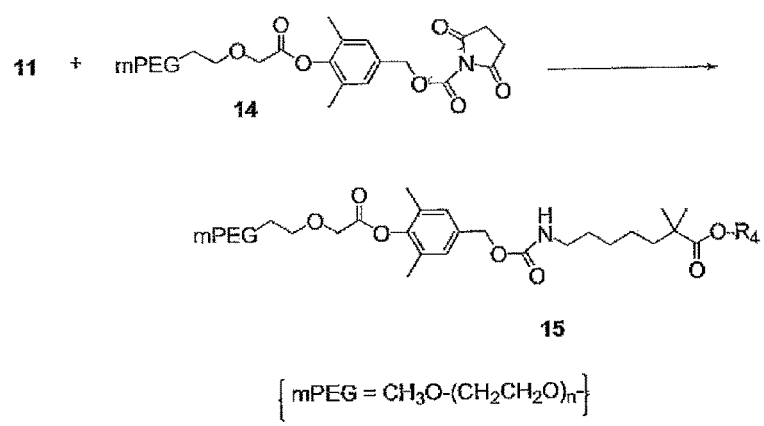
FIG. 2 schematically illustrates methods of synthesis described in Example 10.
Figure 3:
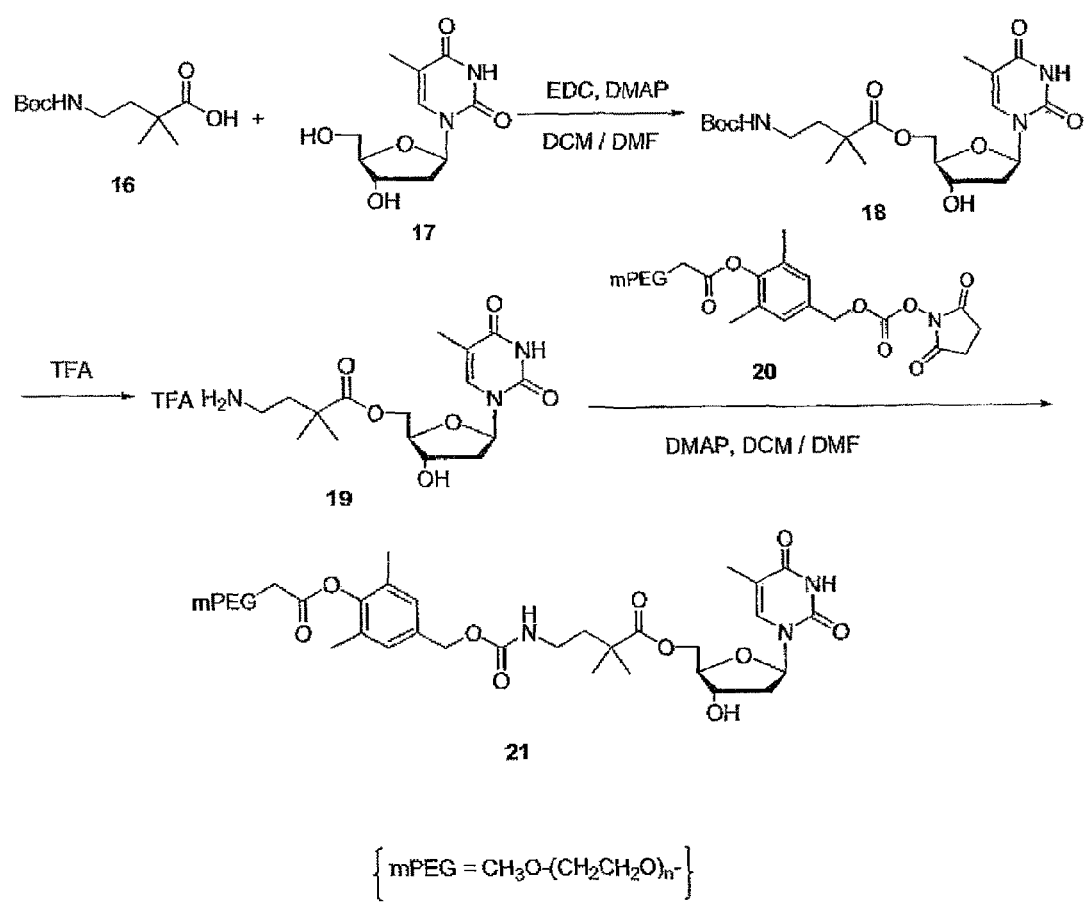
FIG. 3 schematically illustrates methods of synthesis described in Examples 11-13.
Figure 4:
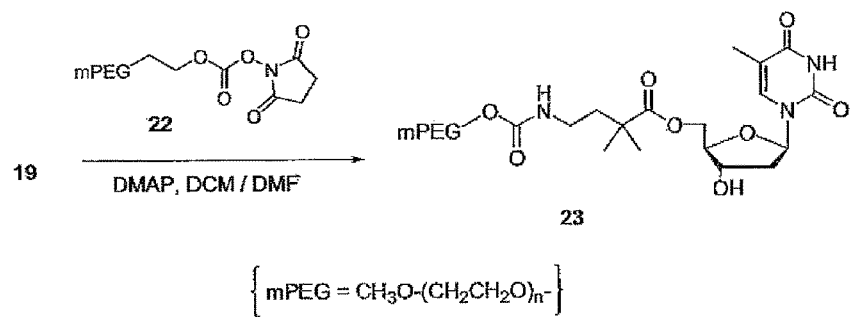
FIG. 4 schematically illustrates methods of synthesis described in Example 14.

The following examples serve to provide further appreciation of the invention hut are not meant in any way to restrict the scope of the invention. The bold-faced numbers recited in the Examples correspond to those shown in FIG. 1-4. Abbreviations are used throughout the examples such as, DCM (dichloromethane), DIPEA (diisopropylethylamine), DMAP (4-dimemylammopyridine), DMF (N,N'-dimethylformamide), EDC (1-(3-dimethylamino-propyl)-3-ethyl carbodiimide), IPA (isopropanol), Mmt (4-memoxytriphenylmethyl), NHS (N-hydroxysuccinimide), PEG (polyethylene glycol), SCA-SH (single-chain antibody), SC-PEG (succinimidyl carbonate polyethylene glycol), TEAA (tetraethylammonium acetate), TFA (trifluoraacetic acid), and THF (tetrahydrofuran).

General Procedures. All reactions are run under an atmosphere of dry nitrogen or argon. Commercial reagents are used without further purification. All PEG compounds are dried under vacuum or by azeotropic distillation from toluene prior to use, $^{13}$C NMR spectra were obtained at 75.46 MHz using a Varian Mercury®300 NMR spectrometer and deuterated chloroform and pyridine as the solvents unless otherwise specified. Chemical shifts (δ) are reported in parts per million (ppm) downfield from tetramethylsilane (TMS).

HPLC Method. The reaction mixtures and the purity of intermediates and final products are monitored by a Beckman Coulter System Gold® HPLC instrument. It employs a ZORBAX® 300SB C8 reversed phase column (150×4.6 mm) or a Phenomenex Jupiter® 300A C18 reversed phase column (150×4.6 mm) with a 168 Diode Array UV Detector, using a gradient of 5-80% of acetonitrile in 0.05 M tetraemylarnmonittm acedtate (TFAA) at a flow rate of 1 mL/min.)

Example 1

Preparation of Br-HE-OEt, Compound (3)

Butyllithium (1.6 M solution in t-BuOH, 200 mL) was added to a solution of ethyl isobutyrate (compound 1, 35 g) in THF (500 mL) at −78° C. and the solution was stirred for 1 h at the same temperature, 1,5-Dibromopetane (compound 7, 100 g) was added and the mixture was allowed to warm up to room temperature. The mixture was stirred at room temperature for 1 hour and was poured into aqueous sodium bicarbonate (500 mL). The organic layer was evaporated. The residue was purified by a silica gel column, eluted with 10% ethyl acetate in hexane to give the desired product as a liquid (29.2 g, yield 36.7%).

Example 2

Preparation of $N_3$—HE-OEt, Compound (4)

Ethyl 7-bromo-2,2-dimethylheptanoate (compound 3, 26.5 g) was heated with sodium azide (13 g) in DMF (500 mL) at 100° C. for 2 hours. The mixture was concentrated and the residue was purified by a silica gel column, eluted with 10% ethyl acetate in hexane to give the desired product as a liquid (20.5 g, yield 90.3%).

Example 3

Preparation of $N_3$—HE-OH, Compound (5)

Ethyl 7-azido-2,2-dimethylheptanoate (compound 4, 20.5 g) was heated with sodium hydroxide (10 g, 85%) in ethanol (500 mL) under reflux for 2 hours. The mixture was concentrated and water (400 mL) was added. The mixture was acidified with concentrated hydrochloric acid to pH 2 and extracted with ethyl acetate (500 mL). The organic layer was concentrated and the residue was purified by a silica gel column, eluted with 50% ethyl acetate in hexane to give the desired product as a liquid (17.1 g, yield 95%).

Example 4

Preparation of $N_3$—HE-T, Compound (7)

7-Azido-2,2-dimethylheptanoic acid (compound 5, 8 g) was dissolved in dichloromethane (200 mL). Oxalyl chloride (6.4 g) was added and the mixture was refluxed for 2 h and evaporated. The residue was dissolved in dichloromethane (100 mlL) and was added in 3'-acetyl thymidine (compound 6, 5.85 g) in pyridine (100 mL). The solution was stirred at room temperature for 24 hours and was poured into aqueous sodium bicarbonate (500 mL). The mixture was extracted with dichloromethane (500 mL) and the organic layer was concentrated. The residue was purified by a silica gel column, eluted with 5% methanol in DCM to give the desired product as a colorless solid (5.6 g, yield 61%).

Example 5

Preparation of $NH_2$—HE-T, Compound (8)

5'-(7-Azido-2,2-dimethymeptanoyl) 3'-acetylthymidine (compound 7, 4.65 g) was hydrogenated in methanol (200 mL) under 30 psi in the presence of Pd/C (10%, 0.5 g) for 1 h. The mixture was filtered and the filtrate was evaporated to give a solid (4.4 g, yield 100%).

Example 6

Preparation of MmtNH—HE-T, Compound (9)

5'-(7-Ammo-2,2-dimethylheptanoyl) 3'-acetylthymidine (compound 8, 4.4 g), triethylamine (4 ml) and 4-methoxytrityl chloride (7.5 g) were stirred in pyridine (100 mL) for 10 h. Methylamine (40%, 10 mL) was added and the solution was stirred for 2 h. The mixture was poured into aqueous sodium bicarbonate (500 mL) and extracted with dichloromethane (500 mL). The organic layer was concentrated. The residue was purified by a silica gel column, eluted with 5% methanol in dichloromethane to give the desired product as a colorless solid (4.9 g, yield 71%).

Example 7

Preparation of MmtNH—HE-T-Phosphoroamidite, Compound (10)

5'-(7-[(MMT-ammo)-2,2-dimethylheptanoyl] thymidine (Compound 9, 4.9 g), N,N-tetraisopropyl-cyanoethyl phosphoramidite (3 g) and tetrazole (0.5 g) in acetonitrile (50 ml) was stirred overnight. The mixture was poured into aqueous sodium bicarbonate (500 ml) and extracted with dichloromethane (500 ml). The organic layer was concentrated. The residue was purified by a silica gel column, eluted with 50% ethyl acetate in hexane to give the desired product as a colorless solid (4.5 g, yield 71%).

Example 8

Preparation of $NH_2$—HE-Oligo, Compounds (11)

Compound 10 was transferred to Trilink Biotechnologies, CA to use as the last monomer in the oligo synthesis. The Mmt group was deprotected after the synthesis and the oligo was purified by RP-HPLC and compound 11 as the free amine was obtained for PEG conjugation. The sequence of oligonucleotide was TCTCCCAGCGTGCGCCAT (SEQ ID NO. 4).

Example 9

Preparation of PEG-HE-Oligo, Compounds (13)

To a solution of compound 11 (10 mg, 1.7 μmol) in PBS buffer (5 mL, pH 7.8) was added SC-PEG (compound 12, Mw 30 kDa, 520 mg, 17 μmol) and stirred at room temperature for 5 hrs. The reaction mixture was diluted to 50 mL with water and loaded on a Poros HQ, strong anion exchange column (10 mm×1.5 mm, bed volume ~16 mL) which was pre-equilibrated with 20 mM Tris-HCl buffer, pH 7.4 (buffer A). The column was washed with 3-4 column volumes of buffer A to remove the excess PEG linker. Then the product was eluted with a gradient of 0 to 100% 1 M NaCl in 20 mM Tris-HCl buffer, pH 7.4, buffer B in 10 min, followed by 100% buffer B for 10 min at a flow rate of 10 mL/min. The eluted product was desalted using HiPrep desalting column (50 mL) and lyophilized to give 6 mg of the product. The equivalent of oligonucleotide in the conjugate measured by UV was 60%, wt/wt.

Example 10

Preparation of PEG-Linker-HE-Oligo Compound (15)

To a solution of compound 11 (10 mg, 1.7 µmol) in PBS buffer (5 mL, pH 7.8) was added PEG-Linker-NHS (compound 14, Mw 30 kDa, 520 mg, 17 µmol) and stirred at room temperature for 5 hrs. The reaction mixture was diluted to 50 mL with water and loaded on a Poros HQ, strong anion exchange column (10 mm×1.5 mm, bed volume ~16 mL) which was pre-equilibrated with 20 mM Tris-HCl buffer, pH 7.4 (buffer A). The column was washed with 3-4 column volumes of buffer A to remove the excess PEG linker. Then the product was eluted with a gradient of 0 to 100% 1 M NaCl in 20 mM Tris-HCl buffer, pH 7.4, buffer B in 10 min, followed by 100% buffer B for 10 min at a flow rate of 10 mL/min. The eluted product was desalted using HiPrep desalting column (50 mL) and lyophilized to solid to give 5 mg of the desired product. The equivalent of oligonucleotide in the conjugate measured by UV was 50%, wt/wt.

Example 11

Preparation of BocNH-BM, Compound (18)

4-Boc-ammo-2,2-dimethybutyric acid (compound 16, 0.50 g, 2.16 mmol) was dissolved in a mixture of chloroform (10 mL) and DMF (5 mL), and thymidine (compound 17, 0.79 g, 3.25 mmol) was added. The reaction mixture was cooled in an ice bath, and EDC (0.62 g, 3.25 mmol) was added, followed by DMAP (0.40 g, 3.25 mmol). The reaction mixture was allowed to warm to room temperature for 20 hours with stirring. Solvent was removed in vacuo and the residue was suspended in ethyl acetate, washed with 0.1N HCl, and brine. Organic layer was dried over anhydrous sodium sulfate and the solvent was removed in vacuo to give a crude oil. Flash column chromatography on silica gel using DCM/EtOAc (40:60, v/v) gave 0.28 g of the desired product: $^{13}$C NMR d 177.21, 164.08, 156.41, 150.80, 135.46, 111,49, 85.43, 84.30, 80.21, 71.28, 63.77, 41.67, 41.08, 40.00, 37.69, 36.99, 28.87, 26.14, 25.55, 13.06.

Example 12

Preparation of $NH_2$—HE-T, Compounds (19)

Compound 18 (0.25 g, 0.55 mmol) was dissolved in DCM (5 mL), and TFA (0.25 mL) was added to the solution via a pipette at room temperature. The reaction mixture was stirred at room temperature for 20 minutes. Solvents and TFA were removed in vacuo by co-evaporating with DCM to remove TFA completely and to give 0.32 g of the product as a glassy solid: $^{13}$C NMR ($CD_3CN$) d 176.61, 164.22, 150.81, 136.41, 136.18, 110.82, 85.14, 85.07, 84.14, 83.97, 70.99, 64.56, 41.32, 39.35, 37.13, 36.92, 25.10, 24.92, 24.75, 12.08, 11.98.

Example 13

Preparation of PEG-HEX, Compounds (21)

mPEG-Linker-NHS (compound 20, Mw. 20 k, 0.50 g, 0.0246 mmol) and compound 19 (26 mg, 0.0738 mmol) were dissolved in a mixture of DCM (5 mL) and DMF (1 mL), and DMAP (15 mg, 0.0123 mmol) was added to the solution. Reaction mixture was stirred at room temperature for 2.5 hours. Solvent was removed in vacuo, and the crude product was precipitated by the addition of ethyl ether. The solid was collected by filtration and recrystallized from acetonitrile/IPA to give 0.43 g of the product as pure white solid: $^{13}$C NMR d 177.9, 168.0, 164.0, 150.9, 134.9, 133.1, 129.8, 128.1, 110.2, 84.4, 83.9, 70.4, 67.8, 64.5, 63.2, 60.0, 58.7, 40.1, 39.4, 37.2, 25.2, 24.7, 16.1, 12.2.

Example 14

Preparation of PEG-HE-T, Compounds (23)

mPEG-NHS (compound 22, Mw. 20 k, 1 g, 0.0492 mmol) and compound 19 (26 mg, 0.1476 mmol) were dissolved in a mixture of DCM (10 mL) and DMF (2 mL), and DMAP (30 mg, 0.246 mmol) was added to the solution. Reaction mixture was stirred at room temperature for 2.5 hours. Solvent was removed in vacuo, and the crude product was precipitated by the addition of ethyl ether. The solid was collected by filtration and recrystallized from acetonitrile/IPA to give 0.90 g of the product as a white solid: $^{13}$C NMR d 178.2, 162.9, 156.0, 149.5, 134.6, 110.3, 84.4, 83.4, 70.1, 69.1, 64.4, 63.5, 62.6, 61.2, 58.6, 40.6, 40.0, 39.4, 37.1, 12.2.

Example 15

Determination of Stability of PEG Conjugates in Buffer and Rat Plasma

The rates of hydrolysis were obtained by employing a C8 reversed phase column (Zorbax® SB-C8) using a gradient mobile phase consisting of (a) 0.1 M triethylammonium acetate buffer and (b) acetonitrile. A flow rate of 1 mL/min was used, and chromatograms were monitored using a UV detector at 227 nm for paclitaxel and 260 nm for oligonucleotides. For hydrolysis in buffer, PEG derivatives were dissolved in 0.1 M pH 7.4 PBS or water at a concentration of 5 mg/mL, while for hydrolysis in plasma, the derivatives were dissolved in distilled water at a concentration of 20 mg/100 µL and 900 µL of rat plasma was added to this solution. The mixture was vortexed for 2 min and divided into 2 mL glass vials with 100 µL of the aliquot per each vial. The solutions were incubated at 37° C. for various periods of time. A mixture of methanol-acetonitrile (1:1, v/v, 400 µL) was added to a vial at the proper interval and the mixture was vortexed for 1 min, followed by filtration through 0.45 mm filter membrane (optionally followed by a second filtration through 0.2 mm filter membrane). An aliquot of 20 µL of the filtrate was injected into the HPLC. On the basis of the peak area, the amounts of native compound and PEG derivative were estimated, and the half-life of each compound in different media was calculated using linear regression analysis from the disappearance of PEG derivative. The results of the stability study for compounds in the examples are set forth in Table 1.

TABLE 1

Result of Stability Study of PEG conjugates

| Compound | $t_{1/2}$ in PBS (h) | $t_{1/2}$ in rat plasma (h) |
|---|---|---|
| Compound 13 | >24 | >24 |
| Compound 15 | >24 | 16.0 |

I claim:

1. A compound of Formula (I)

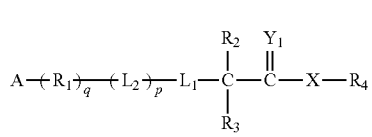

wherein

A is a capping group or

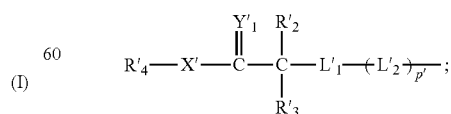

$R_1$ is a polyalkylene oxide;

$L_1$ and $L'_1$ —$NR_{11}(CR_{12}R_{13})_s$, wherein $R_{11-13}$ are H and s is 5;

$L_2$ and $L'_2$ are independently selected bifunctional linkers of formula

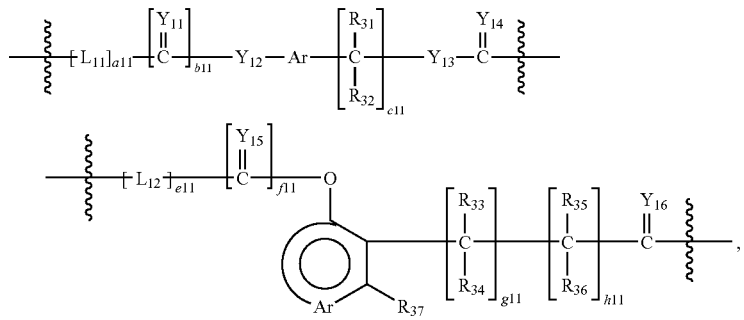

wherein $Y_{11-14}$ are O, a11, b11, and c11 are each 1, $R_{31-32}$ are each H, Ar is

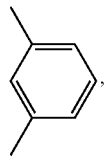

and $L_{11}$ is a bifunctional spacer of formula $-[C(=O)]_v(CR_{22}R_{23})_t[C(=O)]_{v'}-$, wherein v and v' are zero, t is 1, and $R_{22-23}$ are H;

$Y_1$ and $Y'_1$ are independently O, or S;

X and X' are independently O or S;

$R_2$, $R'_2$, $R_3$, $R'_3$ are methyl;

$R_4$ and $R'_4$ are independently selected polynucleotides;

(p) and (p') are independently 1;

(q) and (q') are independently 1; and the capping group is $C_{1-6}$ alkyl.

2. The compound of claim 1, wherein $R_4$ and $R'_4$ are independently selected oligonucleotides.

3. The compound of claim 1, wherein $R_4$ and $R'_4$ are independently selected from the group consisting of sense oligonucleotides, antisense oligonucleotides, locked nucleic acids (LNA), short interfering RNA (siRNA), microRNA (miRNA), aptamers, peptide nucleic acid (PNA), phosphorodiamidate morpholino oligonucleotides (PMO), tricyclo-DNA, double stranded oligonucleotide (decoy ODN), catalytic RNA (RNAi), aptamers, spiegelmers, CpG oligomers and in combination.

4. The compound of claim 1, wherein $R_4$ and $R'_4$ independently comprise ribonucleic acids, deoxyribonucleic acids, or in combination.

5. The compound of claim 1, wherein $R_4$ and $R'_4$ are independently single stranded oligonucleotides or double stranded nucleotides.

6. The compound of claim 1, wherein $R_4$ and $R'_4$ independently comprise phosphorodiester backbone or phosphorothioate backbone.

7. The compound of claim 1, wherein $R_1$ comprises a linear, terminally branched or multi-armed polyalkylene oxide.

8. The compound of claim 7, wherein the polyalkylene oxide is selected from the group consisting of polyethylene glycol and polypropylene glycol.

9. The compound of claim 7, wherein the polyalkylene oxide is selected from the group consisting of $-Y_{71}-(CH_2CH_2O)_n-CH_2CH_2Y_{71}-$, $-Y_{71}-(CH_2CH_2O)_n-CH_2C(=Y_{22})-Y_{71}-$, $-Y_{71}-C(=Y_{72})-(CH_2)_{a2}-Y_{73}-(CH_2CH_2O)_n-CH_2CH_2-Y_{73}-(CH_2)_{a2}-C(=Y_{72})-Y_{71}-$ and $-Y_{71}-(CR_{71}R_{72})_{a2}-Y_{73}-(CH_2)_{b2}-O-(CH_2CH_2O)_n-(CH_2)_{b2}-Y_{73}-(CR_{71}R_{72})_{a2}-Y_{71}-$, wherein:

$Y_{71}$ and $Y_{73}$ are independently O, S, SO, $SO_2$, $NR_{73}$ or a bond;

$Y_{72}$ is O, S, Or $NR_{74}$;

$R_{71-74}$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

(a2) and (b2) are independently zero or a positive integer; and (n) is an integer from about 10 to about 2300.

10. The compound of claim 7, wherein the polyalkylene oxide is a polyethylene glycol of the formula, $-O-(CH_2CH_2O)_n-$ wherein (n) is an integer from about 10 to about 2,300.

11. The compound of claim 1, wherein $R_1$ has an average molecular weight from about 2,000 to about 100,000 daltons.

12. The compound of claim 1, wherein $R_1$ has an average molecular weight of from about 5,000 to about 60,000 daltons.

13. The compound of claim 1, wherein $R_1$ has an average molecular weight from about 5,000 to about 25,000 daltons or from about 20,000 to about 45,000 daltons.

14. The compound of claim 1 selected from the group consisting of:

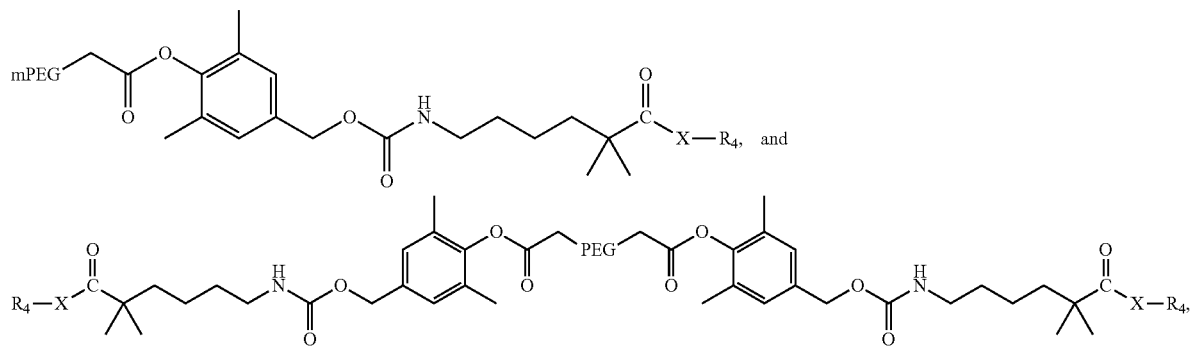

wherein:

$R_4$ is a polynucleotide;

mPEG has the formula: $CH_3—O(CH_2CH_2O)_n—$;

PEG has the formula $—O(CH_2CH_2O)_n—$; and (n) is a positive integer from about 10 to about 2,300.

15. The compound of claim 1 wherein $R_4$ and $R'_4$ are independently selected from the group consisting of SEQ ID NO: 1, SEQ ID NOs: 2 and 3, SEQ ID NO: 4, and SEQ ID NO: 5.

16. A method of preparing a hindered acyl or ester moiety-containing polymeric conjugate of Formula (I) of claim 1 comprising:

reacting a compound of Formula (VI):

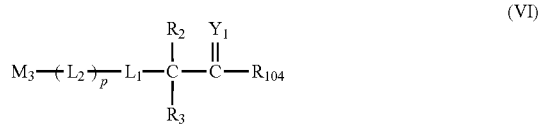

(VI)

with a compound of Formula (VII):

$A_4\text{-}R_1\text{-}M_4$ (VII)

under conditions sufficient to form a compound of Formula (VIII):

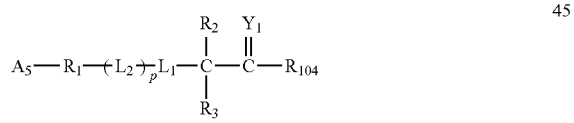

wherein $A_4$ is a capping group or $M_4$;

$A_5$ is a capping group or

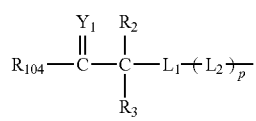

$M_3$ is —OH, SH, or —$NHR_{105}$;

$M_4$ is a leaving group selected from the group consisting of halogens, activated carbonates, isocyanate, N-hydroxysuccinimidyl, tosylate, mesylate, tresylate, nosylate, ortho-nitrophenoxy, and imidazole and;

$R_{104}$ is a polynucleotide;

$R_{105}$ is selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy;

$L_1$ is $NR_{11}(CR_{12}R_{13})_s$—, wherein $R_{11-13}$ are H and s is 5;

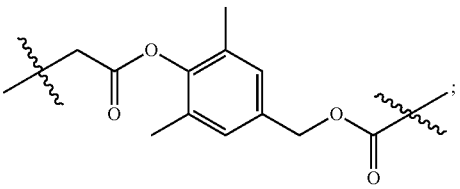

$L_2$ is $Y_1$ is O, S, or $NR_5$;

X is O or S;

(p) is 1;

(q) is 1; and the capping group is $C_{1-6}$ alkyl.

* * * * *

UNITED STATES PATENT AND TRADEMARK OFFICE
CERTIFICATE OF CORRECTION

PATENT NO. : 8,110,559 B2
APPLICATION NO. : 12/402743
DATED : February 7, 2012
INVENTOR(S) : Hong Zhao Page 1 of 1

It is certified that error appears in the above-identified patent and that said Letters Patent is hereby corrected as shown below:

Correct the following:

a) Column 49, line 4, in claim 1, delete the following formula

" 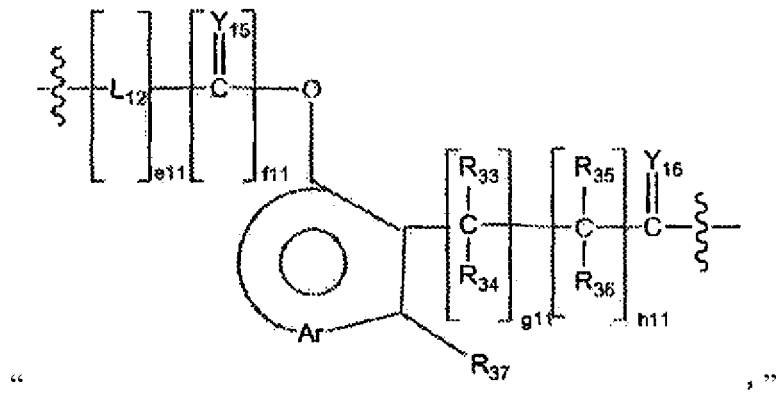 , "

b) Column 52, line 22, in claim 16,

"ortho-nitrophenoxy, and imidazole and;" should read --ortho-nitrophenoxy, and imidazole;--

Signed and Sealed this
Eighth Day of May, 2012

David J. Kappos
*Director of the United States Patent and Trademark Office*